US008815818B2

(12) United States Patent
Samarsky et al.

(10) Patent No.: US 8,815,818 B2
(45) Date of Patent: Aug. 26, 2014

(54) PHAGOCYTIC CELL DELIVERY OF RNAI

(75) Inventors: Dmitry Samarsky, Westborough, MA (US); Tod M. Woolf, Sudbury, MA (US)

(73) Assignee: RXi Pharmaceuticals Corporation, Marlborough, MA (US)

( * ) Notice: Subject to any disclaimer, the term of this patent is extended or adjusted under 35 U.S.C. 154(b) by 30 days.

(21) Appl. No.: 13/054,696

(22) PCT Filed: Jul. 17, 2009

(86) PCT No.: PCT/US2009/004144
§ 371 (c)(1),
(2), (4) Date: Jun. 6, 2011

(87) PCT Pub. No.: WO2010/008582
PCT Pub. Date: Jan. 21, 2010

(65) Prior Publication Data
US 2012/0016005 A1    Jan. 19, 2012

Related U.S. Application Data

(60) Provisional application No. 61/135,244, filed on Jul. 18, 2008.

(51) Int. Cl.
*C12N 15/11* (2006.01)
(52) U.S. Cl.
USPC ............................................... 514/44 A
(58) Field of Classification Search
USPC ............................................... 514/44 A
See application file for complete search history.

(56) References Cited

U.S. PATENT DOCUMENTS

| | | |
|---|---|---|
| 3,373,337 A | 3/1968 | Hung et al. |
| 3,687,808 A | 8/1972 | Merigan et al. |
| 3,737,337 A | 6/1973 | Schnoring et al. |
| 3,891,570 A | 6/1975 | Fukushima et al. |
| 4,201,860 A | 5/1980 | Naito et al. |
| 4,235,871 A | 11/1980 | Papahadjopoulos et al. |
| 4,384,975 A | 5/1983 | Fong |
| 4,389,330 A | 6/1983 | Tice et al. |
| 4,415,732 A | 11/1983 | Caruthers et al. |
| 4,426,330 A | 1/1984 | Sears |
| 4,501,728 A | 2/1985 | Geho et al. |
| 4,652,441 A | 3/1987 | Okada et al. |
| 4,737,323 A | 4/1988 | Martin et al. |
| 4,810,646 A | 3/1989 | Jamas et al. |
| 4,837,028 A | 6/1989 | Allen |
| 4,897,355 A | 1/1990 | Eppstein et al. |
| 4,904,582 A | 2/1990 | Tullis |
| 4,958,013 A | 9/1990 | Letsinger |
| 4,992,540 A | 2/1991 | Jamas et al. |
| 5,013,556 A | 5/1991 | Woodle et al. |
| 5,023,243 A | 6/1991 | Tullis |
| 5,028,703 A | 7/1991 | Jamas et al. |
| 5,032,401 A | 7/1991 | Jamas et al. |
| 5,051,257 A | 9/1991 | Pietronigro |
| 5,053,228 A | 10/1991 | Mori et al. |
| 5,082,936 A | 1/1992 | Jamas et al. |
| 5,108,921 A | 4/1992 | Low et al. |
| 5,112,963 A | 5/1992 | Pieles et al. |
| 5,149,782 A | 9/1992 | Chang et al. |
| 5,151,510 A | 9/1992 | Stec et al. |
| 5,162,115 A | 11/1992 | Pietronigro |
| 5,188,897 A | 2/1993 | Suhadolnik et al. |
| 5,213,804 A | 5/1993 | Martin et al. |
| 5,227,170 A | 7/1993 | Sullivan |
| 5,264,221 A | 11/1993 | Tagawa et al. |
| 5,264,423 A | 11/1993 | Cohen et al. |
| 5,264,562 A | 11/1993 | Matteucci |
| 5,322,841 A | 6/1994 | Jamas et al. |
| 5,354,844 A | 10/1994 | Beug et al. |
| 5,356,633 A | 10/1994 | Woodle et al. |
| 5,395,619 A | 3/1995 | Zalipsky et al. |
| 5,401,727 A | 3/1995 | Rorstad et al. |
| 5,405,939 A | 4/1995 | Suhadolnik et al. |
| 5,407,609 A | 4/1995 | Tice et al. |
| 5,416,016 A | 5/1995 | Low et al. |
| 5,416,203 A | 5/1995 | Letsinger |
| 5,417,978 A | 5/1995 | Tari et al. |
| 5,432,272 A | 7/1995 | Benner |
| 5,453,496 A | 9/1995 | Caruthers et al. |
| 5,459,127 A | 10/1995 | Felgner et al. |
| 5,459,255 A | 10/1995 | Cook et al. |

(Continued)

FOREIGN PATENT DOCUMENTS

| | | |
|---|---|---|
| AU | 2004206255 B2 | 8/2004 |
| CN | 1 568 373 A | 1/2005 |

(Continued)

OTHER PUBLICATIONS

Beier et al., Kinetics of particle uptake in the domes of Peyer's patches. Am J Physiol. Jul. 1998;275(1 Pt 1):G130-7.

Bjergarde et al., Solid phase synthesis of oligodeoxyribonucleoside phosphorodithioates from thiophosphoramidites. Nucleic Acids Res. Nov. 11, 1991;19(21):5843-50.

Bonfils et al., Drug targeting: synthesis and endocytosis of oligonucleotide-neoglycoprotein conjugates. Nucleic Acids Res. Sep. 11, 1992;20(17):4621-9.

Bonfils et al., Uptake by macrophages of a biotinylated oligo-alpha-deoxythymidylate by using mannosylated streptavidin. Bioconjug Chem. Jul.-Aug. 1992;3(4):277-84.

(Continued)

*Primary Examiner* — Brian Whiteman

(74) *Attorney, Agent, or Firm* — Wolf, Greenfield & Sacks, P.C.

(57) ABSTRACT

The present invention provides a particulate delivery system for delivering an RNAi construct to phagocytic cells such as macrophages, comprising various configurations of a complex comprising a phagocytic cell-targeting moiety and an RNAi construct. The invention further provides methods of making the delivery system, and their uses, such as treating phagocytic cell-associated disease conditions.

17 Claims, No Drawings

(56) References Cited

U.S. PATENT DOCUMENTS

| | | |
|---|---|---|
| 5,466,786 A | 11/1995 | Buhr et al. |
| 5,469,854 A | 11/1995 | Unger et al. |
| 5,470,967 A | 11/1995 | Huie et al. |
| 5,486,603 A | 1/1996 | Buhr |
| 5,489,677 A | 2/1996 | Sanghvi et al. |
| 5,495,009 A | 2/1996 | Matteucci et al. |
| 5,504,079 A | 4/1996 | Jamas et al. |
| 5,512,295 A | 4/1996 | Kornberg et al. |
| 5,512,439 A | 4/1996 | Hornes et al. |
| 5,514,786 A | 5/1996 | Cook et al. |
| 5,525,465 A | 6/1996 | Haralambidis et al. |
| 5,527,528 A | 6/1996 | Allen et al. |
| 5,532,130 A | 7/1996 | Alul |
| 5,534,259 A | 7/1996 | Zalipsky et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,561,225 A | 10/1996 | Maddry et al. |
| 5,574,142 A | 11/1996 | Meyer, Jr. et al. |
| 5,578,718 A | 11/1996 | Cook et al. |
| 5,580,575 A | 12/1996 | Unger et al. |
| 5,580,731 A | 12/1996 | Chang et al. |
| 5,580,972 A | 12/1996 | Tu et al. |
| 5,583,020 A | 12/1996 | Sullivan |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |
| 5,594,121 A | 1/1997 | Froehler et al. |
| 5,595,756 A | 1/1997 | Bally et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,677 A | 3/1997 | Jamas et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,658,731 A | 8/1997 | Sproat et al. |
| 5,661,025 A | 8/1997 | Szoka, Jr. et al. |
| 5,661,134 A | 8/1997 | Cook et al. |
| 5,663,312 A | 9/1997 | Chaturvedula |
| 5,670,633 A | 9/1997 | Cook et al. |
| 5,672,662 A | 9/1997 | Harris et al. |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| 5,466,786 B1 | 4/1998 | Buhr et al. |
| 5,736,392 A | 4/1998 | Hawley-Nelson et al. |
| 5,750,666 A | 5/1998 | Caruthers et al. |
| 5,767,099 A | 6/1998 | Harris et al. |
| 5,770,713 A | 6/1998 | Imbach et al. |
| 5,777,153 A | 7/1998 | Lin et al. |
| 5,780,053 A | 7/1998 | Ashley et al. |
| 5,789,416 A | 8/1998 | Lum et al. |
| 5,792,847 A | 8/1998 | Buhr et al. |
| 5,808,023 A | 9/1998 | Sanghvi et al. |
| 5,817,781 A | 10/1998 | Swaminathan et al. |
| 5,830,430 A | 11/1998 | Unger et al. |
| 5,830,653 A | 11/1998 | Froehler et al. |
| 5,851,548 A | 12/1998 | Dattagupta et al. |
| 5,855,910 A | 1/1999 | Ashley et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,968,811 A | 10/1999 | Greenshields |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,094 A | 12/1999 | Simon et al. |
| 6,005,096 A | 12/1999 | Matteucci et al. |
| 6,015,886 A | 1/2000 | Dale et al. |
| 6,020,475 A | 2/2000 | Capaldi et al. |
| 6,020,483 A | 2/2000 | Beckvermit et al. |
| 6,025,140 A | 2/2000 | Langel et al. |
| 6,028,183 A | 2/2000 | Lin et al. |
| 6,043,352 A | 3/2000 | Manoharan et al. |
| 6,051,699 A | 4/2000 | Ravikumar |
| 6,107,094 A | 8/2000 | Crooke |
| 6,111,085 A | 8/2000 | Cook et al. |
| 6,121,437 A | 9/2000 | Guzaev et al. |
| 6,133,229 A | 10/2000 | Gibson et al. |
| 6,153,737 A | 11/2000 | Manoharan et al. |
| 6,207,819 B1 | 3/2001 | Manoharan et al. |
| 6,242,594 B1 | 6/2001 | Kelly |
| 6,271,358 B1 | 8/2001 | Manoharan et al. |
| 6,300,319 B1 | 10/2001 | Manoharan |
| 6,326,358 B1 | 12/2001 | Manoharan |
| 6,331,617 B1 | 12/2001 | Weeks et al. |
| 6,335,434 B1 | 1/2002 | Guzaev et al. |
| 6,344,436 B1 | 2/2002 | Smith et al. |
| 6,355,787 B1 | 3/2002 | Beckvermit et al. |
| 6,358,931 B1 | 3/2002 | Cook et al. |
| 6,372,499 B1 | 4/2002 | Midoux et al. |
| 6,379,965 B1 | 4/2002 | Boutin |
| 6,395,492 B1 | 5/2002 | Manoharan et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,440,943 B1 | 8/2002 | Cook et al. |
| 6,444,448 B1 | 9/2002 | Wheatcroft et al. |
| 6,444,806 B1 | 9/2002 | Veerapanani et al. |
| 6,465,628 B1 | 10/2002 | Ravikumar et al. |
| 6,476,003 B1 | 11/2002 | Jordan et al. |
| 6,476,205 B1 | 11/2002 | Buhr et al. |
| 6,506,559 B1 | 1/2003 | Fire et al. |
| 6,525,031 B2 | 2/2003 | Manoharan |
| 6,528,631 B1 | 3/2003 | Cook et al. |
| 6,531,584 B1 | 3/2003 | Cook et al. |
| 6,559,279 B1 | 5/2003 | Manoharan et al. |
| 6,656,730 B1 | 12/2003 | Manoharan |
| 6,673,611 B2 | 1/2004 | Thompson et al. |
| 6,683,167 B2 | 1/2004 | Metelev et al. |
| 6,815,432 B2 | 11/2004 | Wheeler et al. |
| 6,849,726 B2 | 2/2005 | Usman et al. |
| 6,858,225 B2 | 2/2005 | Semple et al. |
| 6,887,906 B1 | 5/2005 | Teng et al. |
| 7,041,824 B2 | 5/2006 | Bordon-Pallier et al. |
| 7,056,704 B2 | 6/2006 | Tuschl et al. |
| 7,078,196 B2 | 7/2006 | Tuschl et al. |
| 7,205,297 B2 | 4/2007 | Beauchamp et al. |
| 7,432,250 B2 | 10/2008 | Crooke |
| 7,538,095 B2 | 5/2009 | Fire et al. |
| 7,560,438 B2 | 7/2009 | Fire et al. |
| 7,595,387 B2 | 9/2009 | Leake et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,829,693 B2 | 11/2010 | Kreutzer et al. |
| 8,110,674 B2 | 2/2012 | Manoharan et al. |
| 8,263,569 B2 | 9/2012 | Baulcombe et al. |
| 2002/0081736 A1 | 6/2002 | Conroy et al. |
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0027780 A1 | 2/2003 | Hardee et al. |
| 2003/0077829 A1 | 4/2003 | MacLachlan |

(56) References Cited

U.S. PATENT DOCUMENTS

| | | |
|---|---|---|
| 2003/0108923 A1 | 6/2003 | Tuschl et al. |
| 2003/0139585 A1 | 7/2003 | Uhlmann et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2003/0216346 A1 | 11/2003 | Sakurai et al. |
| 2004/0009938 A1 | 1/2004 | Manoharan et al. |
| 2004/0014715 A1 | 1/2004 | Ostroff |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0072785 A1 | 4/2004 | Wolff et al. |
| 2004/0137471 A1 | 7/2004 | Vickers et al. |
| 2004/0162235 A1 | 8/2004 | Trubetskoy et al. |
| 2004/0167090 A1 | 8/2004 | Monahan et al. |
| 2004/0171033 A1 | 9/2004 | Baker et al. |
| 2004/0180351 A1 | 9/2004 | Giese et al. |
| 2004/0192629 A1 | 9/2004 | Xu et al. |
| 2004/0204377 A1 | 10/2004 | Rana |
| 2004/0219520 A1 | 11/2004 | Mirkin et al. |
| 2004/0229266 A1 | 11/2004 | Tuschl et al. |
| 2004/0248839 A1 | 12/2004 | Kowalik |
| 2004/0259247 A1 | 12/2004 | Tuschl et al. |
| 2005/0020521 A1 | 1/2005 | Rana |
| 2005/0032733 A1 | 2/2005 | McSwiggen et al. |
| 2005/0037496 A1 | 2/2005 | Rozema et al. |
| 2005/0064595 A1 | 3/2005 | MacLachlan et al. |
| 2005/0080246 A1 | 4/2005 | Allerson et al. |
| 2005/0107325 A1 | 5/2005 | Manoharan et al. |
| 2005/0142535 A1 | 6/2005 | Damha et al. |
| 2005/0175682 A1 | 8/2005 | Heyes et al. |
| 2005/0181382 A1 | 8/2005 | Zamore et al. |
| 2005/0255487 A1 | 11/2005 | Khvorova et al. |
| 2005/0265957 A1 | 12/2005 | Monahan et al. |
| 2005/0281781 A1* | 12/2005 | Ostroff ............... 424/93.2 |
| 2006/0008910 A1 | 1/2006 | MacLachlan et al. |
| 2006/0009409 A1* | 1/2006 | Woolf ............... 514/44 |
| 2006/0035344 A1 | 2/2006 | Pachuk et al. |
| 2006/0160766 A1 | 7/2006 | Cheung |
| 2006/0178324 A1 | 8/2006 | Hadwiger et al. |
| 2006/0178327 A1 | 8/2006 | Yeung |
| 2006/0188506 A1 | 8/2006 | Cheung |
| 2006/0240093 A1 | 10/2006 | MacLachlan et al. |
| 2007/0032441 A1 | 2/2007 | McSwiggen et al. |
| 2007/0166734 A1* | 7/2007 | Bhat et al. ............... 435/6 |
| 2007/0173473 A1 | 7/2007 | McSwiggen et al. |
| 2007/0173476 A1 | 7/2007 | Leake et al. |
| 2007/0231392 A1 | 10/2007 | Wagner et al. |
| 2007/0269889 A1 | 11/2007 | Leake et al. |
| 2008/0038296 A1 | 2/2008 | Brahmbhatt et al. |
| 2008/0071068 A1 | 3/2008 | Oba et al. |
| 2008/0085869 A1 | 4/2008 | Yamada et al. |
| 2008/0152661 A1 | 6/2008 | Rozema et al. |
| 2008/0311040 A1 | 12/2008 | Berry et al. |
| 2009/0131360 A1 | 5/2009 | Woolf et al. |
| 2009/0171075 A1 | 7/2009 | Li |
| 2009/0186802 A1 | 7/2009 | Alluis et al. |
| 2010/0040656 A1 | 2/2010 | Franklin et al. |
| 2010/0069620 A1 | 3/2010 | Zon |
| 2010/0136695 A1* | 6/2010 | Woolf ............... 435/461 |
| 2011/0039914 A1 | 2/2011 | Pavco et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0040459 A1 | 2/2012 | Khvorova et al. |
| 2012/0059046 A1 | 3/2012 | Woolf et al. |
| 2012/0065243 A1 | 3/2012 | Woolf et al. |
| 2013/0131141 A1 | 5/2013 | Khvorova et al. |
| 2013/0131142 A1 | 5/2013 | Libertine et al. |
| 2013/0197055 A1 | 8/2013 | Kamens et al. |

FOREIGN PATENT DOCUMENTS

| | | |
|---|---|---|
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 1/2010 |
| JP | 4 095 895 B2 | 9/2004 |
| WO | WO 90/14074 A1 | 11/1990 |
| WO | WO 91/16024 A1 | 10/1991 |
| WO | WO 91/17424 A1 | 11/1991 |
| WO | WO 92/03464 A1 | 3/1992 |
| WO | WO 94/23028 A1 | 10/1994 |
| WO | WO 95/11910 A1 | 5/1995 |
| WO | WO 95/23162 A1 | 8/1995 |
| WO | WO 96/40964 A2 | 12/1996 |
| WO | WO 99/13915 A1 | 3/1999 |
| WO | WO 00/03683 A2 | 1/2000 |
| WO | WO 02/12348 A2 | 2/2002 |
| WO | WO 03/012052 A2 | 2/2003 |
| WO | WO 2004/065600 A2 | 8/2004 |
| WO | WO 2004/065601 A2 | 8/2004 |
| WO | WO 2004/090105 A2 | 10/2004 |
| WO | WO 2005/018544 A2 | 3/2005 |
| WO | WO 2005/019430 A2 | 3/2005 |
| WO | WO 2005/019453 A2 | 3/2005 |
| WO | WO 2005/024033 A2 | 3/2005 |
| WO | WO 2005/079533 A2 | 9/2005 |
| WO | WO 2005/097992 A2 | 10/2005 |
| WO | WO 2006/007372 A2 | 1/2006 |
| WO | WO 2006/019430 A2 | 2/2006 |
| WO | WO 2006/032039 A2 | 3/2006 |
| WO | WO 2006/039656 A2 | 4/2006 |
| WO | WO 2006/065601 A2 | 6/2006 |
| WO | WO 2006/113679 A2 | 10/2006 |
| WO | WO 2006/128141 A2 | 11/2006 |
| WO | WO 2007/021142 A1 | 2/2007 |
| WO | WO 2007/030167 A1 | 3/2007 |
| WO | WO 2007/050643 A2 | 5/2007 |
| WO | WO 2007/089607 A2 | 8/2007 |
| WO | WO 2008/021157 A1 | 2/2008 |
| WO | WO 2008/036825 A2 | 3/2008 |
| WO | WO 2008/109353 A1 | 9/2008 |
| WO | WO 2009/005813 A1 | 1/2009 |
| WO | WO 2009/126933 A2 | 10/2009 |
| WO | WO 2010/006237 A2 | 1/2010 |
| WO | WO 2010/027830 A2 | 3/2010 |
| WO | WO 2010/042281 A2 | 4/2010 |
| WO | WO 2010/135207 A1 | 11/2010 |
| WO | WO 2011/109698 A1 | 9/2011 |

OTHER PUBLICATIONS

Boussif et al., Optimized galenics improve in vitro gene transfer with cationic molecules up to 1000-fold. Gene Ther. Dec. 1996;3(12):1074-80.

Brown et al., Immune recognition. A new receptor for beta-glucans. Nature. Sep. 6, 2001;413(6851):36-7.

Clark et al., Exploiting M cells for drug and vaccine delivery. Adv Drug Deliv Rev. Aug. 23, 2001;50(1-2):81-106.

Clark et al., Targeting polymerised liposome vaccine carriers to intestinal M cells. Vaccine. Oct. 12, 2002;20(1-2):208-17.

Diebold et al., Mannose receptor-mediated gene delivery into antigen presenting dendritic cells. Somat Cell Mol Genet. Nov. 2002;27(1-6):65-74. Review.

Fajac et al., Uptake of plasmid/glycosylated polymer complexes and gene transfer efficiency in differentiated airway epithelial cells. J Gene Med. 2003;5(1):38-48.

Felgner et al., Lipofection: a highly efficient, lipid-mediated DNA-transfection procedure. Proc Natl Acad Sci U S A. Nov. 1987;84(21):7413-7.

Floch et al., Cationic phosphonolipids as non viral vectors for DNA transfection in hematopoietic cell lines and CD34+ cells. Blood Cells Mol Dis. 1997;23(1):69-87.

Florence, The oral absorption of micro- and nanoparticulates: neither exceptional nor unusual. Pharm Res. Mar. 1997;14(3):259-66.

(56) References Cited

OTHER PUBLICATIONS

Fritz et al., Gene transfer into mammalian cells using histone-condensed plasmid DNA. Hum Gene Ther. Aug. 1, 1996;7(12):1395-404.
Fuhrhop et al., Bolaamphiphiles with mannose- and tetraalkylammonium head groups as coatings for nucleic acids and possible reagents for transfections. Chem Phys Lipids. 1987;43(3):193-213.
Funhoff et al., Endosomal escape of polymeric gene delivery complexes is not always enhanced by polymers buffering at low pH. Biomacromolecules. Jan.-Feb. 2004;5(1):32-9.
Giaimis et al., Both mannose and beta-glucan receptors are involved in phagocytosis of unopsonized, heat-killed *Saccharomyces cerevisiae* by murine macrophages. J Leukoc Biol. Dec. 1993;54(6):564-71.
Goldman et al., in vitro and in vivo gene delivery mediated by a synthetic polycationic amino polymer. Nat Biotechnol. May 1997;15(5):462-6.
Gottschalk et al., A novel DNA-peptide complex for efficient gene transfer and expression in mammalian cells. Gene Ther. May 1996;3(5):448-57.
Grosse et al., In vivo gene delivery in the mouse lung with lactosylated polyethylenimine, questioning the relevance of in vitro experiments. J Control Release. Dec. 8, 2008;132(2):105-12. Epub Sep. 4, 2008.
Haensler et al., Polyamidoamine cascade polymers mediate efficient transfection of cells in culture. Bioconjug Chem. Sep.-Oct. 1993;4(5):372-9.
Hashimoto et al., Gene transfer by DNA/mannosylated chitosan complexes into mouse peritoneal macrophages. Biotechnol Lett. Jun. 2006;28(11):815-21. Epub May 31, 2006.
Henderson et al., Rapid recruitment of inflammatory monocytes is independent of neutrophil migration. Blood. Jul. 1, 2003;102(1):328-35. Epub Mar. 6, 2003.
Ihre et al., Fast and convenient divergent synthesis of aliphatic ester dendrimers by anhydride coupling. J Am Chem Soc. Jun. 27, 2001;123(25):5908-17.
Jablonski et al., Preparation of oligodeoxynucleotide-alkaline phosphatase conjugates and their use as hybridization probes. Nucleic Acids Res. Aug. 11, 1986;14(15):6115-28.
Kichler, Gene transfer with modified polyethylenimines. J Gene Med. Feb. 2004;6 Suppl 1:S3-10. Review.
Legendre et al., Dioleoylmelittin as a novel serum-insensitive reagent for efficient transfection of mammalian cells. Bioconjug Chem. Jan.-Feb. 1997;8(1):57-63.
Liu et al., Unique expression of suppressor of cytokine signaling 3 is essential for classical macrophage activation in rodents in vitro and in vivo. J Immunol. May 1, 2008;180(9):6270-8.
Martinez-Pomares et al., Analysis of mannose receptor regulation by IL-4, IL-10, and proteolytic processing using novel monoclonal antibodies. J Leukoc Biol. May 2003;73(5):604-13.
Mistry et al., Recombinant HMG1 protein produced in *Pichia pastoris*: a nonviral gene delivery agent. Biotechniques. Apr. 1997;22(4):718-29.
Muller et al., Functional beta-glucan receptor expression by a microglial cell line. Res Immunol. May 1994;145(4):267-75.
Murphy et al., A combinatorial approach to the discovery of efficient cationic peptoid reagents for gene delivery. Proc Natl Acad Sci U S A. Feb. 17, 1998;95(4):1517-22.
Nakase et al., Biodegradable microspheres targeting mucosal immune-regulating cells: new approach for treatment of inflammatory bowel disease. J Gastroenterol. Mar. 2003;38 Suppl 15:59-62.
Park et al., Mannosylated polyethylenimine coupled mesoporous silica nanoparticles for receptor-mediated gene delivery. Int J Pharm. Jul. 9, 2008;359(1-2):280-7. Epub Apr. 12, 2008.
Ross et al., Specificity of membrane complement receptor type three (CR3) for beta-glucans. Complement. 1987;4(2):61-74.
Tamilarasu et al., Targeting RNA with peptidomimetic oligomers in human cells. Bioorg Med Chem Lett. Feb. 26, 2001;11(4):505-7.
Tamilarasu et al., High affinity and specific binding of HIV-1 TAR RNA by a tat-derived oligourea. J. Am. Chem. Soc. 1999; 121(7):pp. 1597-1598.
Tang et al., In vitro gene delivery by degraded polyamidoamine dendrimers. Bioconjug Chem. Nov.-Dec. 1996;7(6):703-14.
Taylor et al., Pattern recognition receptors and differentiation antigens define murine myeloid cell heterogeneity ex vivo. Eur J Immunol. Aug. 2003;33(8):2090-7.
Taylor et al., The beta-glucan receptor, dectin-1, is predominantly expressed on the surface of cells of the monocyte/macrophage and neutrophil lineages. J Immunol. Oct. 1, 2002;169(7):3876-82.
Uhlmann et al., Antisense oligonucleotides: a new therapeutic principle. Chem Rev. 1990;90(4):543-84.
Wadhwa Peptide-mediated gene delivery: influence of peptide structure on gene expression. Bioconjug Chem. Jan.-Feb. 1997;8(1):81-8.
Wagner et al., DNA-binding transferrin conjugates as functional gene-delivery agents: synthesis by linkage of polylysine or ethidium homodimer to the transferrin carbohydrate moiety. Bioconjug Chem. Jul.-Aug. 1991;2(4):226-31.
Wu et al., Receptor-mediated in vitro gene transformation by a soluble DNA carrier system. J Biol Chem. Apr. 5, 1987;262(10):4429-32. Erratum in: J Biol Chem Jan. 5, 1988;263(1):588.
Wyman et al., Design, synthesis, and characterization of a cationic peptide that binds to nucleic acids and permeabilizes bilayers. Biochemistry. Mar. 11, 1997;36(10):3008-17.
Zhou et al., Controlled release of PEI/DNA complexes from mannose-bearing chitosan microspheres as a potent delivery system to enhance immune response to HBV DNA vaccine. J Control Release. Aug. 28, 2007;121(3):200-7. Epub May 25, 2007.
Zimmerman et al., A novel carbohydrate-glycosphingolipid interaction between a beta-(1-1)-glucan immunomodulator, PGG-glucan, and lactosylceramide of human leukocytes. J. Biol Chem. Aug. 21, 1998;273(34):22014-20.
[No Author Listed] RedChip Small-Cap Investor Conference. RXI Pharmaceuticals (Nasdaq RXII). Jun. 16, 2009 Presentation. 5 pages.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Akinc et al., Development of lipidoid-siRNA formulations for systemic delivery to the liver. Mol Ther. May 2009;17(5):872-9. doi: 10.1038/mt.2009.36. Epub Mar. 3, 2009.
Aleckovic et al., RNAi at Oxford. J RNAi Gene Silencing. May 27, 2008;4(1):266-8.
Aouadi et al., Orally delivered siRNA targeting macrophage Map4k4 suppresses systemic inflammation. Nature. Apr. 30, 2009;458(7242):1180-4. doi: 10.1038/nature07774.
Baigude et al., Design and creation of new nanomaterials for therapeutic RNAi. ACS Chem Biol. Apr. 24, 2007;2(4):237-41.
Bongartz et al., Improved biological activity of antisense oligonucleotides conjugated to a fusogenic peptide. Nucleic Acids Res. Nov. 11, 1994;22(22):4681-8.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
Braasch et al., RNA Interference in Mammalian Cells by Chemically-Modified RNA. Biochem. 2003;42(26):7967-75.
Brown et al., Light at the end of the tunnel. J RNAi Gene Silencing. Jul. 28, 2006;2(2):175-7.
Chiu et al., siRNA function in RNAi: a chemical modification analysis. RNA. Sep. 2003;9(9):1034-48.
Choung et al. Chemical modification of siRNAs to improve serum stability without loss of efficacy. Biochem Biophys Res Commun. Apr. 14, 2006;342(3):919-27.
Constantinides et al., Formulation and intestinal absorption enhancement evaluation of water-in-oil microemulsions incorporating medium-chain glycerides. Pharm Res. Oct. 1994;11(10):1385-90.
Crombez et al., A non-covalent peptide-based strategy for siRNA delivery. Biochem Soc Trans. Feb. 2007;35(Pt 1):44-6.
Czauderna et al., Structural variations and stabilising modifications of synthetic siRNAs in mammalian cells. Nucleic Acids Res. Jun. 1, 2003;31(11):2705-16.

(56) References Cited

OTHER PUBLICATIONS

De Smidt et al., Association of antisense oligonucleotides with lipoproteins prolongs the plasma half-life and modifies the tissue distribution. Nucleic Acids Res. Sep. 11, 1991;19(17):4695-700.
Debart et al., Chemical modifications to improve the cellular uptake of oligonucleotides. Curr Top Med Chem. 2007;7(7):727-37.
Dykxhoorn et al., The silent treatment: siRNAs as small molecule drugs. Gene Ther. Mar. 2006;13(6):541-52.
Elbashir et al., Functional anatomy of siRNAs for mediating efficient RNAi in *Drosophila melanogaster* embryo lysate. EMBO J. Dec. 3, 2001;20(23):6877-88.
Fedorov et al., Off-target effects by siRNA can induce toxic phenotype. RNA. Jul. 2006;12(7):1188-96. Epub May 8, 2006.
Ferentz et al., Disulfide-crosslinked oligonucleotides. Journal of the American Chemical Society. 1991;113 (10): 4000-4002.
Frank-Kamenetsky et al., Therapeutic RNAi targeting PCSK9 acutely lowers plasma cholesterol in rodents and LDL cholesterol in nonhuman primates. Proc Natl Acad Sci U S A. Aug. 19, 2008;105(33):11915-20. Epub Aug. 11, 2008.
Ginobbi et al., Folic acid-polylysine carrier improves efficacy of c-myc antisense oligodeoxynucleotides on human melanoma (M14) cells. Anticancer Res. Jan.-Feb. 1997;17(1A):29-35.
Ho et al., Preparation of microemulsions using polyglycerol fatty acid esters as surfactant for the delivery of protein drugs. J Pharm Sci. Feb. 1996;85(2):138-43.
Hope et al., Cationic lipids, phosphatidylethanolamine and the intracellular delivery of polymeric, nucleic acid-based drugs (review). Mol Membr Biol.; Jan.-Mar. 1998;15(1):1-14.
Huang et al., Lipitoids—novel cationic lipids for cellular delivery of plasmid DNA in vitro. Chem Biol. Jun. 1998;5(6):345-54.
Jackson et al., Position-specific chemical modification of siRNAs reduces "off-target" transcript silencing. RNA. Jul. 2006;12(7):1197-1205. Epub May 8, 2006.
Jäschke et al., Automated Incorporation of Polyethylene Glycol into Synthetic Oligonucleotides, Tetra. Lett. Jan. 1993;34(2):301-304.
Jiang et al., Mannosylated chitosan-graft-polyethylenimine as a gene carrier for Raw 264.7 cell targeting. Int J Pharm. Jun. 22, 2009;375(1-2):133-9. Epub Apr. 5, 2009.
Kamata et al., Amphiphilic peptides enhance the efficiency of liposome-mediated DNA transfection. Nucleic Acids Res. Feb. 11, 1994;22(3):536-7.
Kim et al., Synthetic dsRNA Dicer substrates enhance RNAi potency and efficacy. Nat Biotechnol. Feb. 2005;23(2):222-6. Epub Dec. 26, 2004.
Kim et al., Systemic and specific delivery of small interfering RNAs to the liver mediated by apolipoprotein A-I. Mol Ther. Jun. 2007;15(6):1145-52. Epub Apr. 17, 2007.
Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Kubo et al., Modified 27-nt dsRNAs with dramatically enhanced stability in serum and long-term RNAi activity. Oligonucleotides. 2007 Winter;17(4):445-64.
Layzer et al., In vivo activity of nuclease-resistant siRNAs. RNA. May 2004;10(5):766-71.
Lemaitre et al., Specific antiviral activity of a poly(L-lysine)-conjugated oligodeoxyribonucleotide sequence complementary to vesicular stomatitis virus N protein mRNA initiation site. Proc Natl Acad Sci U S A. Feb. 1987;84(3):648-52.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Leuschner et al., Cleavage of the siRNA passenger strand during RISC assembly in human cells. EMBO Rep. Mar. 2006;7(3):314-20. Epub Jan. 20, 2006.
Lewis et al., A serum-resistant cytofectin for cellular delivery of antisense oligodeoxynucleotides and plasmid DNA. Proc Natl Acad Sci U S A. Apr. 16, 1996;93(8):3176-81.

Li et al., Surface-modified LPD nanoparticles for tumor targeting. Ann N Y Acad Sci. Oct. 2006;1082:1-8.
Li et al., Yeast glucan particles activate murine resident macrophages to secrete proinflammatory cytokines via MyD88- and Syk kinase-dependent pathways. Clin Immunol. Aug. 2007;124(2):170-81. Epub Jun. 14, 2007.
Liang et al., Oligonucleotide delivery: a cellular prospective. Pharmazie Aug. 1999;54(8):559-66.
Macrae et al., Structure of Dicer and mechanistic implications for RNAi. Cold Spring Harb Symp Quant Biol. 2006;71:73-80.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.
Martins et al., Sterol side chain length and structure affect the clearance of chylomicron-like lipid emulsions in rats and mice. J Lipid Res. Feb. 1998;39(2):302-12.
Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.
Medarova et al., In vivo imaging of siRNA delivery and silencing in tumors. Nat Med. Mar. 2007;13(3):372-7. Epub Feb. 25, 2007.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.
Milhem et al., Polyamidoamine Starburst dendrimers as solubility enhancers. Int J Pharm. Mar. 20, 2000;197(1-2):239-41.
Murchison et al., Characterization of Dicer-deficient murine embryonic stem cells. Proc Natl Acad Sci U S A. Aug. 23, 2005;102(34):12135-40. Epub Aug. 12, 2005.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Olejnik et al., Photocleavable biotin phosphoramidite for 5'-end-labeling, affinity purification and phosphorylation of synthetic oligonucleotides. Nucleic Acids Res. Jan. 15, 1996;24(2):361-6.
Overhoff et al., Phosphorothioate-stimulated uptake of short interfering RNA by human cells. EMBO Rep. Dec. 2005;6(12):1176-81.
Parrish et al., Functional anatomy of a dsRNA trigger: differential requirement for the two trigger strands in RNA interference. Mol Cell. Nov. 2000;6(5):1077-87.
Rajeev et al., 2'-modified-2-thiothymidine oligonucleotides. Org Lett. Aug. 21, 2003;5(17):3005-8.
Rozema et al., Dynamic PolyConjugates for targeted in vivo delivery of siRNA to hepatocytes. Proc Natl Acad Sci U S A. Aug. 7, 2007;104(32):12982-7. Epub Jul. 24, 2007.
Rump et al., Preparation of conjugates of oligodeoxynucleotides and lipid structures and their interaction with low-density lipoprotein. Bioconjug Chem. May-Jun. 1998;9(3):341-9.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Schaniel et al., Delivery of short hairpin RNAs—triggers of gene silencing—into mouse embryonic stem cells. Nat Methods. May 2006;3(5):397-400.
Schell et al., Stimulation of the uptake of polynucleotides by poly(L-lysine). Biochim Biophys Acta. Mar. 27, 1974;340(3):323-33.
Seela et al., Oligodeoxyribonucleotides containing 1,3-propanediol as nucleoside substitute. Nucleic Acids Res. Apr. 10, 1987;15(7):3113-29.
Shen, Advances in the development of siRNA-based therapeutics for cancer. IDrugs. Aug. 2008;11(8):572-8. Review.
Shi, Mammalian RNAi for the masses. Trends Genet. Jan. 2003;19(1):9-12.
Soto et al., Oral Macrophage Mediated Gene Delivery System. 2007 NSTI Nanotechnology Conference and Trade Show, May 20-24, 2007, Santa Clara, CA. NSTI Nanotech 2007 Proceedings; 2:378-81.

(56) References Cited

OTHER PUBLICATIONS

Soto et al., Characterization of multilayered nanoparticles encapsulated in yeast cell wall particles for DNA delivery. Bioconjug Chem. Apr. 2008;19(4):840-8. doi: 10.1021/bc700329p. Epub Apr. 1, 2008.
Soutschek et al., Therapeutic silencing of an endogenous gene by systemic administration of modified siRNAs. Nature. Nov. 11, 2004;432(7014):173-8.
Sui et al., A DNA vector-based RNAi technology to suppress gene expression in mammalian cells. Proc Natl Acad Sci U S A. Apr. 16, 2002;99(8):5515-20.
Tan et al., Quantum-dot based nanoparticles for targeted silencing of HER2/neu gene via RNA interference. Biomaterials. Mar. 2007;28(8):1565-71. Epub Dec. 11, 2006.
Van Der Lubben et al., Transport of chitosan microparticles for mucosal vaccine delivery in a human intestinal M-cell model. J Drug Target Sep. 2002;10(6):449-56.
Vlassov et al., Transport of oligonucleotides across natural and model membranes. Biochim Biophys Acta. Jun. 29, 1994;1197(2):95-108.
Wagner et al., Transferrin-polycation-DNA complexes: the effect of polycations on the structure of the complex and DNA delivery to cells. Proc Natl Acad Sci U S A. May 15, 1991;88(10):4255-9.
Wolfrum et al., Mechanisms and optimization of in vivo delivery of lipophilic siRNAs. Nat Biotechnol. Oct. 2007;25(10):1149-57. Epub Sep. 16, 2007.
Yamada et al., Tranilast, a selective inhibitor of collagen synthesis in human skin fibroblasts. J Biochem. Oct. 1994;116(4):892-7.
Yu et al., RNS interference by expression of short-interfering RNAs and hairpin RNAs in mammalian cells. Proc Natl Acad Sci U S A. Apr. 30, 2002;99(9):6047-52. Epub Apr. 23, 2002.
Zhou et al., Lipophilic polylysines mediate efficient DNA transfection in mammalian cells. Biochim Biophys Acta. May 31, 1991;1065(1):8-14.
Zimmermann et al., RNAi-mediated gene silencing in non-human prim ates. Nature. May 4, 2006;441(7089):111-4. Epub Mar. 26, 2006.

\* cited by examiner

SEQUENCE LISTING

```
<160> NUMBER OF SEQ ID NOS: 14

<210> SEQ ID NO 1
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 1

Cys Cys Tyr Gly Arg Lys Lys Arg Arg Gln Arg Arg Arg
1               5                   10

<210> SEQ ID NO 2
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 2

Arg Arg Arg Arg Arg Arg Arg Arg Arg
1               5
```

```
<210> SEQ ID NO 3
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 3

Arg Lys Lys Arg Arg Gln Arg Arg Pro Pro Gln Cys
1               5                   10

<210> SEQ ID NO 4
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 4

Cys Tyr Gln Arg Lys Lys Arg Arg Gln Arg Arg Arg
1               5                   10

<210> SEQ ID NO 5
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 5

Arg Gln Ile Lys Ile Trp Phe Gln Asn Arg Arg Met Lys Trp Lys Lys
1               5                   10                  15

Gly Gly Cys

<210> SEQ ID NO 6
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 6

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 7
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 7

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 8
<211> LENGTH: 27
<212> TYPE: PRT
<213> ORGANISM: Artificial sequence
```

<220> FEATURE:
<223> OTHER INFORMATION: Synthetic polypeptide

<400> SEQUENCE: 8

Gly Ala Leu Phe Leu Gly Trp Leu Gly Ala Ala Gly Ser Thr Met Gly
1               5                   10                  15

Ala Trp Ser Gln Pro Lys Lys Arg Lys Val
            20                  25

<210> SEQ ID NO 9
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 27
<212> TYPE: PRT
<213> ORGANISM: Artificial sequence
<220> FEATURE:
<223> OTHER INFORMATION: Synthetic polypeptide

<400> SEQUENCE: 11

Gly Ala Leu Phe Leu Gly Trp Leu Gly Ala Ala Gly Ser Thr Met Gly
1               5                   10                  15

Ala Trp Ser Gln Pro Lys Lys Arg Lys Val
            20                  25

<210> SEQ ID NO 12
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 12

Ala Ala Val Ala Leu Leu Pro Ala Val Leu Leu Ala Leu Leu Ala Pro
1               5                   10                  15

<210> SEQ ID NO 13
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 13

Gly Trp Thr Leu Asn Ser Ala Gly Tyr Leu Leu Lys Ile Asn Leu Lys
1               5                   10                  15

```
Ala Leu Ala Ala Leu Ala Lys Lys Ile Leu
            20                  25

<210> SEQ ID NO 14
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 14

Lys Leu Ala Leu Lys Leu Ala Leu Lys Ala Leu Lys Ala Ala Leu Lys
1               5                   10                  15

Leu Ala
```

PHAGOCYTIC CELL DELIVERY OF RNAI

RELATED APPLICATIONS

This application is a national stage filing under 35 U.S.C. §371 of international application PCT/US2009/004144, filed Jul. 17, 2009, which was published under PCT Article 21(2) in English, and claims the benefit under 35 U.S.C. §119(e) of U.S. Provisional Application Ser. No. 61/135,244, filed Jul. 18, 2008, the disclosures of which are incorporated by reference herein in their entireties.

FIELD OF THE INVENTION

This invention relates, in part, to delivery systems for delivering RNA molecules to phagocytic cells.

BACKGROUND OF THE INVENTION

Drug delivery systems are designed to provide a biocompatible reservoir of an active agent, preferably for controlled release of the active agent dependent either on time, or on local conditions, such as pH. While macroscopic drug delivery systems such as transdermal patches, implantable osmotic pumps and implantable subcutaneous depots (e.g., NORPLANT™) have had some success, there has been continuing interest in microscopic drug delivery systems such as microcapsules, microparticles and liposomes.

Microcapsules and microspheres are usually powders consisting of spherical particles 2 millimeters (2 mm) or less in diameter, usually 500 microns or less in diameter. If the particles are less than 1 micron, they are often referred to as nanocapsules or nanospheres. A description of methods of making and using microspheres and microcapsules can be found, for example in U.S. Pat. No. 5,407,609 (incorporated by reference). Microcapsules and microspheres can be distinguished from each other by whether the active agent is formed into a central core surrounded by an encapsulating structure, such as a polymeric membrane, or whether the active agent is dispersed throughout the particle; that is, the internal structure is a matrix of the agent and excipient, usually a polymeric excipient. The release of the active agent from a microcapsule is often regulated by the biodegradation of the matrix material, usually a biodegradable polymeric material such as either poly(DL-lactide) (DL-PL) or poly (DL-lactide-co-glycolide) (DL-PLG) as the polymeric excipient.

Liposomes can be considered microcapsules in which the active agent core is encompassed by a lipid membrane instead of a polymeric membrane. Liposomes are artificial lipid vesicles consisting of lipid layers, where the antigen may be encapsulated inside the aqueous compartment of the liposome, or associated with the antigen on the surface via surface-coupling techniques. Liposomes can be prepared easily and inexpensively on a large scale and under conditions that are mild to entrapped antigens. They do not induce immune responses to themselves, and are used in humans for parenterally administered drugs.

While the high surface area/volume ratio of microcapsules, microspheres and liposomes favor the release of the active agent, their small size may provide challenges in manufacturing. A wide variety of methods to prepare microcapsules and microspheres are described in the literature, e.g., U.S. Pat. No.5,407,609 (incorporated by reference). Several of these methods make use of emulsions to make microspheres, in particular to make microspheres less than 2 millimeters in diameter. To give a general example of such processes, one can dissolve a polymer in a suitable organic solvent (the polymer solvent), dissolve or disperse an agent in this polymer solution, disperse the resulting polymer/agent mixture into an aqueous phase (the processing medium) to obtain an oil-in-water emulsion with oil microdroplets dispersed in the processing medium, and remove the solvent from the microdroplets to form microspheres. These processes can also be performed with water-in-oil emulsions and with double emulsions. The use of emulsion-based processes that follow this basic approach is described in several U.S. patents, such as U.S. Pat. Nos. 3,737,337, 3,891,570, 4,384,975, 4,389,330,and 4,652,441 (all incorporated by reference). Additional delivery systems are described in US 2005/0281781 A1 and WO06/007372 (all incorporated herein by reference).

However, there is still a need to develop additional microscopic drug delivery systems capable of selectively or specifically deliver the active agents to specific tissue/cells, preferably delivery systems suitable for delivering specific active agents, such as the various RNAi constructs, via oral or intramuscular injection.

SUMMARY OF THE INVENTION

One aspect of the invention provides a delivery system for delivering an RNAi construct to a phagocytic cell, such as a macrophage or macrophage-like cell, comprising a complex comprising: (a) a phagocytic cell-targeting moiety conjugated with an RNAi construct, wherein the phagocytic cell-targeting moiety comprises beta-glucan and one or more ligands for phagocytic cell receptor(s), wherein the RNAi construct is conjugated to a nanotransporter or a nanoparticle, PEI, a carrier RNA core, or forms a core, and wherein the phagocytic cell-targeting moiety facilitates phagocytosis of the complex by the phagocytic cell; or (b) the RNAi construct conjugated to the nanotransporter or nanoparticle, PEI, or the carrier RNA core, wherein the complex is of sufficient size for phagocytosis by the phagocytic cell.

In other aspects the invention is a delivery system complex comprising an RNAi construct conjugated to a nanotransporter or nanoparticle, PEI, or a carrier RNA core, and a phagocytic cell-targeting moiety conjugated to the RNAi construct, wherein the phagocytic cell-targeting moiety comprises beta-glucan and/or one or more ligands for phagocytic cell receptor(s) and wherein the phagocytic cell-targeting moiety facilitates phagocytosis of the complex by the phagocytic cell; wherein the complex is capable of phagocytosis by the phagocytic cell, and wherein the RNAi construct is not encapsulated or dispersed within the phagocytic cell-targeting moiety.

In yet another aspect the invention is a delivery system complex comprising an RNAi construct conjugated to a nanotransporter or nanoparticle, PEI, or a carrier RNA core, wherein the complex is of sufficient size for phagocytosis by the phagocytic cell.

A delivery system complex comprising a phagocytic cell-targeting moiety conjugated to an RNAi construct, wherein the phagocytic cell-targeting moiety comprises beta-glucan and one or more ligands for phagocytic cell receptor(s) and wherein the phagocytic cell-targeting moiety facilitates phagocytosis of the complex by the phagocytic cell is provided according to other aspects of the invention.

In yet another aspect the invention is a method for delivering an RNAi construct to a phagocytic cell in a subject. The method involves administering a delivery system complex to the subject, wherein the delivery system complex comprises a phagocytic cell-targeting moiety conjugated to an RNAi construct, wherein the RNAi construct is conjugated to a nanotransporter or a nanoparticle, PEI, a carrier RNA core, or forms a core, wherein the RNAi construct is not encapsulated or dispersed within the phagocytic cell-targeting moiety, and wherein the phagocytic cell-targeting moiety facilitates phagocytosis of the complex by the phagocytic cell. In some embodiments the phagocytic cell-targeting moiety is a beta glucan. In other embodiments the phagocytic cell-targeting moiety is one or more ligands for phagocytic cell receptor(s).

The invention, in another aspect, is a method for delivering an RNAi construct to a phagocytic cell in a subject. The method involves administering a delivery system complex to the subject, wherein the delivery system complex comprises a phagocytic cell-targeting moiety conjugated to an RNAi construct, wherein the phagocytic cell-targeting moiety comprises beta-glucan and one or more ligands for phagocytic cell receptor(s), wherein the RNAi construct is conjugated to a nanotransporter or a nanoparticle, PEI, a carrier RNA core, or forms a core, and wherein the phagocytic cell-targeting moiety facilitates phagocytosis of the complex by the phagocytic cell.

In certain embodiments, the RNAi construct is not encapsulated or dispersed within the phagocytic cell-targeting moiety.

In certain embodiments, the beta-glucan may be synthetic, or may be purified/modified from a natural product.

In certain embodiments, the natural product is a yeast. In certain embodiments, the nanoparticle is of the size and/or shape of a bacterium. In certain embodiments, the phagocytic cell-targeting moiety is covalently linked to the RNAi construct.

In certain embodiments, the phagocytic cell-targeting moiety is a ligand that recognizes a pattern-recognition receptor (PRR) selected from mannose receptor (MR), beta-glucan receptor, dectin-1,CR3 (membrane complement receptor type 3), CD36,CD40, CD80,CD86,CCR7,SRB-1,CD14, DEC205,collectins, gp340,MARCO, and Toll-like receptors.

In certain embodiments, the carrier RNA core comprises tRNA.

In certain embodiments, the delivery system further comprises an enteric coating, such as one selected from cellulose acetate phthalate (CAP), hydroxypropyl methylcellulose phthalate (HPMCP), polyvinyl acetate phthalate (PVAP), hydroxypropyl methylcellulose acetate succinate (HPM-CAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, carboxymethyl ethylcellulose, Spheromer III, Spheromer IV, co-polymerized methacrylic acid/methacrylic acid methyl esters selected from: EUDRAGIT® L12.5,L100, EUDRAGIT® S 12.5,S 100,EUDRAGIT® L30D55, EUDRAGIT® FS30D, EUDRAGIT® L100-55, EUDRAGIT® S100 (Rohm Pharma), KOLLICOAT® MAE30D and 30DP (BASF), ESTACRYL® 30D (Eastman Chemical), AQUATERIC® and AQUACOAT® CPD30 (FMC)), Acryl-EZE™ White, or equivalents thereof.

In certain embodiments, the delivery system further comprises a bioadhesive material that selectively adheres to the lower GI tract.

In certain embodiments, the bioadhesive material comprises polymeric materials selected from polyam ides, polyalkylene glycols, polyalkylene oxides, polyvinyl alcohols, polyvinylpyrrolidone, polyglycolides, polyurethanes, polymers of acrylic and methacrylic esters, polylactides, poly(butyric acid), polyanhydrides, polyorthoesters, poly(fumaric acid), poly(maleic acid), polycarbonates, polyalkylenes, polyalkylene terephthalates, polyvinyl alcohols, polyvinyl ethers, polyvinyl esters, polyvinyl halides, polysiloxanes, polystyrene, poly(lactide-co-glycolide), blends and copolymers thereof.

In certain embodiments, the RNAi construct is about 19-49 by in length, about 19-29 by in length, about 19-25 by in length, about 19-23 by in length, about 21-23 by in length, about 25-31 by in length, or about 25-27 by in length.

In certain embodiments, the RNAi construct is double stranded RNA, or a single stranded RNA having a stem-loop or hairpin structure.

In certain embodiments, the RNAi construct has 1, 2, 3,or 4 nucleotide(s) overhang at one or both 3'-ends.

In certain embodiments, the RNAi construct is a Dicer substrate.

In certain embodiments, the RNAi construct is modified on the sugar-phosphate backbone and/or on the base.

In certain embodiments, the RNAi construct is modified on one strand or both strands of the duplex region.

In certain embodiments, the RNAi construct is modified on the sense strand only. In certain embodiments, the RNAi construct is a double-stranded RNA (dsRNA) construct of 19-49 nucleotides in length, for inhibiting expression of a target gene, the dsRNA comprising: (1) a sense strand having a 5'-end and a 3'-end, wherein one or more nucleotides at each of the 5'- and 3'-ends of the sense strand have 2'-modified ribose sugars, and, (2) an antisense strand having a 5'-end and a 3'-end, which hybridizes to the sense strand and to mRNA of the target gene, wherein the antisense strand includes a 2'-modified ribose sugar at the 2nd nucleotide from the 5'-end of the antisense strand, wherein (a) the dsRNA is resistant to cleavage by Dicer, (b) the antisense strand associates with RISC, and (c) the dsRNA inhibits expression of the target gene in a sequence-dependent manner.

In certain embodiments, the RNAi construct is a double-stranded RNA (dsRNA) construct of 19-49 nucleotides in length, for inhibiting expression of a target gene, the dsRNA comprising: (1) a sense strand having a 5'-end and a 3'-end, wherein one or more nucleotides at each of the 5'- and 3'-ends of the sense strand have 2'-modified ribose sugars, and, (2) an antisense strand having a 5'-end and a 3'-end, which hybridizes to the sense strand and to mRNA of the target gene, wherein the antisense strand comprises, at the 3'-end of the antisense strand, (i) at least four consecutive 2'-modified ribose sugars with non-hydrolyzable internucleotide linkages, (ii) 1, 2, 3, 4, 5, 6, 7, 8, 9, 10, 11,or 12 2'-modified ribose sugars, preferably 2'-O-methyl modified ribose sugars, or, (iii) a protective group, wherein (a) the dsRNA is resistant to cleavage by Dicer, (b) the antisense strand associates with RISC, and (c) the dsRNA inhibits expression of the target gene in a sequence-dependent manner.

In certain embodiments, the RNAi construct is a double-stranded RNA (dsRNA) construct of 19-49 nucleotides in length, for inhibiting expression of a target gene, the dsRNA comprising: (1) a sense strand having a 5'-end and a 3'-end, wherein one or more nucleotides at each of the 5'- and 3'-ends of the sense strand have 2'-modified ribose sugars, and the sense strand comprises a mismatch nucleotide at the 2nd nucleotide from the 3'-end of the sense strand, and, (2) an antisense strand having a 5'-end and a 3'-end, which hybridizes to the sense strand and to mRNA of the target gene, wherein (a) the dsRNA is resistant to cleavage by Dicer, (b)

the antisense strand associates with RISC, and (c) the dsRNA inhibits expression of the target gene in a sequence-dependent manner.

In certain embodiments, the RNAi construct is a double-stranded RNA (dsRNA) construct of 19-49 nucleotides in length, for inhibiting expression of a target gene, the dsRNA comprising: (1) a sense strand having a 5'-end and a 3'-end, wherein four consecutive 2'-O-methyl nucleotides are present at each of the 5'- and 3'-ends of the sense strand, and, (2) an antisense strand having a 5'-end and a 3'-end, which hybridizes to the sense strand and to mRNA of the target gene, wherein the antisense strand: (a) comprises four consecutive 2'-O-methyl modified 3'-end nucleotides with phosphothioate linkages; or, (b) comprises a 2'-O-methyl modified nucleotide at the 2nd nucleotide on the 5'-end and no other modified nucleotides, wherein (a) the dsRNA is resistant to cleavage by Dicer, (b) the antisense strand associates with RISC, and (c) the dsRNA inhibits expression of the target gene in a sequence-dependent manner.

In certain embodiments, the RNAi construct is a double-stranded RNA (dsRNA) construct of 19-49 nucleotides in length, for inhibiting expression of a target gene, the dsRNA comprising: (1) a sense strand having a 5'-end and a 3'-end, wherein the sense strand comprises 12 and 10 consecutive 2'-O-methyl nucleotides at the 5'-end and the 3'-end, respectively, and, (2) an antisense strand having a 5'-end and a 3'-end, which hybridizes to the sense strand and to mRNA of the target gene, wherein the antisense strand: (a) is unmodified; (b) comprises four consecutive 2'-O-methyl modified 3'-end nucleotides with phosphothioate linkages; or, (c) comprises a 2'-O-methyl modified nucleotide at the 2nd nucleotide on the 5'-end and no other modified nucleotides, wherein (a) the dsRNA is resistant to cleavage by Dicer, (b) the antisense strand associates with RISC, and (c) the dsRNA inhibits expression of the target gene in a sequence-dependent manner.

In certain embodiments, the antisense strand directs the uniform cleavage of the target gene mRNA at a single site between the 10th and 11th nucleotides from the 5'-end of the antisense strand.

In certain embodiments, the sense strand of the dsRNA is cleavable by RISC at a single site between the 10th and the 11th nucleotides from the 3'-end of the sense strand.

In certain embodiments, the dsRNA construct is blunt-ended.

In certain embodiments, the 5'-end 12 nucleotides and the 3'-end 10 nucleotides of the sense strand are 2'-modified ribose sugars.

In certain embodiments, each end of the sense strand comprises a continuous stretch of 2'-modified ribose sugars.

In certain embodiments, each end of the sense strand comprises a continuous stretch of four 2'-modified ribose sugars.

In certain embodiments, the antisense strand comprises discontinuous 2'-modified ribose sugars, wherein the 10th and 11th antisense nucleotides are not modified.

In certain embodiments, the antisense strand comprises 2'-modified ribose sugars for each 2, 3, 4, 5, 6, 7, 8, or 9 nucleotides.

In certain embodiments, the most 5'-end 2'-modified ribose sugar on the antisense strand is the 2nd nucleotide.

In certain embodiments, the dsRNA construct is: 25-30 nucleotides in length; 25, 26, 27, 28, 29, or 30 nucleotides in length; >22 nucleotides in length; >25 nucleotides in length; or 31-49 nucleotides in length.

In certain embodiments, each end of the sense strand comprises, independently, 4-16 2'-modified ribose sugars and/or non-hydrolyzable internucleotide linkages.

In certain embodiments, each end of the sense strand comprises a symmetrical or an asymmetrical number of 2'-modified ribose sugars.

In certain embodiments, the 2'-modified ribose sugars are 2'-O-alkyl nucleotides, 2'-deoxy-2'-fluoro nucleotides, 2'-deoxy nucleotides, 2'-H (deoxyribonucleotides), or combination thereof.

In certain embodiments, the 2'-O-alkyl nucleotides are 2'-O-methyl nucleotides.

In certain embodiments, the 2'-O-alkyl nucleotides are 2'-O-allyl nucleotides.

In certain embodiments, the antisense strand comprises a 2'-O-methyl modified nucleotide at the 2nd nucleotide on the 5'-end of the antisense strand and no other modified nucleotides.

In certain embodiments, the dsRNA has enhanced target specificity or reduced off-target silencing compared to a similar construct without the 2'-modification at the position(s).

In certain embodiments, the antisense strand comprises at least four consecutive 2'-O-methyl modified 3'-end nucleotides with phosphothioate linkages.

In certain embodiments, the sense strand of the dsRNA comprises a mismatch nucleotide at the 2nd nucleotide from the 3'-end of the sense strand.

In certain embodiments, the dsRNA has improved stability in serum and/or cerebral spinal fluid compared to an unmodified dsRNA having the same sequence.

In certain embodiments, the last 2nd-8th nucleotides at the 3'-end of the sense strand mis-match their corresponding antisense strand nucleotides.

In certain embodiments, the dsRNA does not induce interferon response in primary cells.

In certain embodiments, either end of the sense strand and/or the 3'-end of the antisense strand is blocked by a protective group.

In certain embodiments, the protective group is an inverted nucleotide, an inverted abasic moiety, or an amino-end modified nucleotide.

In certain embodiments, the inverted nucleotide comprises an inverted deoxynucleotide.

In certain embodiments, the inverted abasic moiety comprises an inverted deoxyabasic moiety.

In certain embodiments, the inverted deoxyabasic moiety is a 3',3'-linked or 5',5'-linked deoxyabasic moiety.

In certain embodiments, alternating nucleotides on the ends of the sense and/or antisense strands comprise 2'-modified ribose sugars, and wherein each of the 2'-modified ribose sugars faces an unmodified nucleotide on the opposite strand.

In certain embodiments, the first 2'-modified antisense nucleotide is the most 5'-end antisense nucleotide or the 2nd nucleotide from the 5'-end of the antisense strand.

In another aspect, the invention provides a method of treating an individual for a disease condition associated with a phagocytic cell defect, such as a macrophage defect, comprising administering to the individual a subject delivery system, wherein the RNAi construct antagonizes the function of a target gene causing the disease condition.

In certain embodiments, the target gene is overexpressed in the individual.

In certain embodiments, the disease condition is: macular degeneration, osteoporosis, Crohn's disease, non-immune inflammation, tuberculosis, multiple sclerosis, chronic obstructive pulmonary disease (COPD), Alzheimer's disease, sepsis and septic shock, neutrophilic alveolitis, asthma, hepatitis, inflammatory bowel disease, ischemia/reperfusion, glomerulonephritis, or rheumatoid arthritis.

Another aspect of the invention provides a pharmaceutical composition for oral delivery of an RNAi construct to a phagocytic cell such as a macrophage, comprising any of the subject delivery system, and pharmaceutically acceptable excipients for oral delivery.

Another aspect of the invention provides a pharmaceutical composition for injectable delivery of an RNAi construct to a phagocytic cell such as a macrophage, comprising any of the subject delivery system, and pharmaceutically acceptable excipients for injection.

Another aspect of the invention provides a pharmaceutical package comprising the subject pharmaceutical preparation, in association with instructions (written or pictorial) for administering the preparation to a human patient.

It is contemplated that all embodiments described herein, including those described only under one aspect of the invention, can be combined with any other embodiments wherever applicable.

DETAILED DESCRIPTION OF THE INVENTION

1. Overview

The instant invention is partly based on the discovery that RNAi constructs (including siRNA, microRNA or miRNA, short hairpin RNA or shRNA, and precursors thereof, etc.) can be targeted for selective or even specific delivery to phagocytic cells such as macrophages and macrophage-like cells (such as M cells) through the use of one or more phagocytic cell-targeting moieties. For example, a subject RNAi construct may be conjugated with a carrier, such as a nanotransporter or a nanoparticle, PEI, or a carrier RNA core to form a conjugate, which conjugate is in turn covalently linked to or non-covalently associated with one or more phagocytic cell-targeting moieties, such as beta-glucan and/or one or more ligands for phagocytic cell receptor(s). Alternatively, the subject RNAi construct may be simply conjugated with the carrier (e.g., the nanotransporter or nanoparticle, PEI, or carrier RNA core) to achieve a size sufficiently large for phagocytosis by the phagocytic cells.

Thus in one aspect, the invention provides a delivery system for delivering an RNAi construct to a phagocytic cell, comprising a complex comprising: (a) a phagocytic cell-targeting moiety conjugated with an RNAi construct, wherein the phagocytic cell-targeting moiety comprises beta-glucan and/or one or more ligands for phagocytic cell receptor(s), wherein the RNAi construct is conjugated to a nanotransporter or a nanoparticle, PEI, a carrier RNA core, or forms a core, and wherein the phagocytic cell-targeting moiety facilitates phagocytosis of the complex by the phagocytic cell; or (b) the RNAi construct conjugated to the nanotransporter or nanoparticle, PEI, or the carrier RNA core, wherein the complex is of sufficient size for phagocytosis by the phagocytic cell. Preferably, the delivery system can be formulated for oral delivery or injection.

Aspects of the invention relate to delivering RNA molecules to phagocytic cells. As used herein, a phagocytic cell refers to a cell that can engulf other cells or particles. Several non-limiting examples of phagocytic cells include neutrophils, monocytes, macrophages, dendritic cells, granulocytes and mast cells.

Aspects of the invention relate to phagocytic cell-targeting moieties. As used herein, a phagocytic cell-targeting moiety refers to a molecule that can bind selectively to a phagocytic cell. In some embodiments, a phagocytic cell-targeting moiety is a ligand or an antibody that binds to a receptor on the surface of a phagocytic cell. According to one embodiment of the invention, the RNAi construct being delivered to the cell is not encapsulated or dispersed within the phagocytic cell-targeting moiety. Instead, the RNAi construct simply needs to be linked or conjugated to the phagocytic cell-targeting moiety.

In some embodiments, the phagocytic cell-targeting moiety is a macrophage-targeting moiety. In certain embodiments, the macrophage-targeting moiety selectively binds to macrophages and macrophage-like cells, although the moiety may also bind other non-macrophage cells. For example, the receptors for the macrophage-targeting moiety on the target cell may be enriched on macrophages or similar cells, but may also appear on other cell types, although may be expressed to a lesser degree.

In certain embodiments, the macrophage-targeting moiety selectively binds to macrophages and macrophage-like cells, such that it does not appreciably bind other non-macrophage cells. In other words, the receptors for the macrophage-targeting moiety on the target cell are specifically expressed on macrophages or similar cells.

In some embodiments, the phagocytic cell-targeting moiety is a dendritic cell-targeting moiety. In certain embodiments, the dendritic cell-targeting moiety selectively binds to dendritic and dendritic-like cells, although the moiety may also bind other non-dendritic cells. For example, the receptors for the dendritic cell-targeting moiety on the target cell may be enriched on dendritic cells or similar cells, but may also appear on other cell types, although may be expressed to a lesser degree.

In certain embodiments, the dendritic cell-targeting moiety selectively binds to dendritic cells and dendritic-like cells, such that it does not appreciably bind other non-dendritic cells. In other words, the receptors for the dendritic cell-targeting moiety on the target cell are specifically expressed on dendritic cells or similar cells.

In certain embodiments, the phagocytic cell-targeting moiety is beta-glucan, such as synthetic beta-glucan. The synthesized beta-glucan may be conjugated to a relatively large molecular scaffold, such as a cyclodextran (CD) scaffold, so as to provide a repeat pattern recognizable by the pattern recognition receptors on the macrophage. Alternatively, the beta-glucan may be purified/modified from a natural product, such as a yeast.

In certain embodiments, the phagocytic cell-targeting moiety is a ligand or an antibody that recognizes a receptor such as a pattern-recognition receptor (PRR) on phagocytic cells such as macrophages, macrophage-like cells, dendritic cells, or dendritic-like cells. In some embodiments, the receptor is a C-type lectin receptor such as a mannose receptor (MR), a beta-glucan receptor, dectin-1, CR3 (membrane complement receptor type 3), CD36, CD40, CD80, CD86, CCR7, SRB-1, CD14, DEC205, collectins, gp340, MARCO, and Toll-like receptors.

In certain embodiments, the RNAi may be conjugated to a nanoparticle of a particular size and/or shape to facilitate uptake by phagocytic cells. For example, the nanoparticle may be of the size and/or shape of a bacterium, which may stimulate uptake by phagocytic cells.

In certain embodiments, the RNAi construct may be conjugated to an inert carrier RNA core, such as a core comprising tRNA. In other embodiments, several layers of identical or different RNAi constructs may constitute the core (e.g., no carrier tRNA).

The layered structure of the RNA core (with or without tRNA core) may become sufficiently large (e.g., about 1-10 micron, 10-50 micron etc.) to be non-specifically phagocytosed by phagocytic cells.

In certain embodiments, the phagocytic cell-targeting moiety is covalently linked to the RNAi construct. In other embodiments, the phagocytic cell-targeting moiety is non-covalently associated with the RNAi construct.

A variety of linking groups can be used to connect the substituents of the invention to nucleosides, nucleotides, and/or oligonucleotides. Certain linking groups, such as OMEGA-aminoalkoxy moieties and OMEGA-aminoalkylamino moieties, are particularly useful for linking molecules to the 2'-position of a nucleoside. Many linking groups are commercially available, including heterobifunctional and homobifunctional linking moieties available from the Pierce Co. (Rockford, Ill.). Heterobifunctional and homobifunctional linking moieties are particularly useful in conjunction with the OMEGA-aminoalkoxy and OMEGA-aminoalkylamino moieties to form extended linkers that connect peptides and proteins to nucleosides. Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2,and 3'-Amino-Modifier is also available from Clontech Laboratories Inc. (Palo Alto, Calif). A nucleotide analog bearing a linking group pre-attached to the nucleoside is commercially available from Glen Research Corporation under the tradename "Amino-Modifier-dT." This nucleoside-linking group reagent, a uridine derivative having an [N(7-trifluoroacetylaminoheptyl) 3-acrylamido] substituent group at the 5 position of the pyrimidine ring, is synthesized generally according to Jablonski, et al., Nucleic Acid Research 1986, 14, 6115.It is intended that the nucleoside analogs of the invention include adenine nucleosides functionalized with linkers on their N6 purine amino groups, guanine nucleosides functionalized with linkers at their exocyclic N2 purine amino groups, and cytosine nucleosides functionalized with linkers on either their N4 pyrimidine amino groups or 5 pyrimidine positions.

The RNAi construct or the complex comprising the RNAi construct and the phagocytic cell-targeting moiety may further comprise an enteric coating, such that the RNAi construct may survive the harsh environment of the stomach acid if the delivery system is orally delivered. The presence of the enteric coating also helps to provide controlled release of the RNAi construct in the lower GI portion, optionally with tissue-specific delivery of the RNAi construct.

Exemplary enteric coatings include: cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, carboxymethyl ethylcellulose, Spheromer III, Spheromer IV, co-polymerized methacrylic acid/methacrylic acid methyl esters selected from: EUDRAGIT® L12.5,L100, EUDRAGIT® S12.5,S100,EUDRAGIT® L30D55, EUDRAGIT® FS30D, EUDRAGIT® L100-55, EUDRAGIT® 5100 (Rohm Pharma), KOLLICOAT® MAE3OD and 30DP (BASF), ESTACRYL® 30D (Eastman Chemical), AQUATERIC® and AQUACOAT® CPD30 (FMC)), Acryl-EZE™ White, or equivalents thereof.

Optionally, the subject delivery system may be encapsulated in a capsule or gel cap, which may protect the active ingredients in the stomach, but dissolve or degrade in the intestine. The active ingredient may be solid, or may be liquid suspension.

Optionally, the subject delivery system may be delivered using the ALZET® type mini-osmotic pumps, which are implantable, capsule-shaped units that can deliver solutions containing a wide range of agents at controlled rates for up to several weeks (e.g., 4-6 weeks). The ALZET® type osmotic pumps are commercially available (see, for example, DURECT Corporation, Cupertino, Calif.). They can be orally delivered (e.g., swallowed by patients), or surgically implanted at desired locations. In addition, all pump models are easily attached to a catheter, such that a pump implanted either subcutaneously or intraperitoneally is used to infuse into a vessel, organ or tissue.

The ALZET® type osmotic pumps operate by osmotic displacement. Specifically, an empty reservoir within the core of the pump is filled with the drug or solution to be delivered. Due to the presence of a high concentration of salt in a chamber surrounding the reservoir (but isolated from it by an impermeable layer), water enters the pump through its outer surface (a semipermeable layer). The entry of water increases the volume in the salt chamber, causing compression of the flexible reservoir and delivery of the drug solution into the animal via the exit port. The ALZET® type osmotic pumps require no external connections or user intervention during the entire delivery period, thus eliminating the need for repetitive injection schedules and potential patient non-compliance. These dependable drug delivery systems have proven invaluable in predictably sustaining compounds at therapeutic levels, avoiding potentially toxic or misleading side effects and ensuring accurate therapeutic results.

Because of its mechanism of operation, the ALZET® type osmotic pumps are well suited for administering a wide range of compounds regardless of their molecular weight. Successful delivery of an enormous range of compounds has been reported in the literature, including protein, siRNA, and small molecule chemicals.

An assortment of sizes, flow rates and durations is available to meet a variety of dosage and delivery needs. While the pumping rate of each model is fixed at manufacture, the dose of agent delivered can be adjusted by varying the concentration of agent with which each pump is filled. In addition, multiple pumps may be implanted simultaneously to achieve higher delivery rates than are attainable with a single pump. For more prolonged delivery, pumps may be serially implanted with no ill effects. Published studies have shown infusions of up to 18 months duration with serially implanted pumps, and up to 36 serial implantations have been performed on a single animal.

Optionally, the delivery system may further comprise a bioadhesive material that selectively adheres to a specific target tissue, such as the lower GI tract. Exemplary bioadhesive materials include polyamides, polyalkylene glycols, polyalkylene oxides, polyvinyl alcohols, polyvinylpyrrolidone, polyglycolides, polyurethanes, polymers of acrylic and methacrylic esters, polylactides, poly(butyric acid), polyanhydrides, polyorthoesters, poly(fumaric acid), poly(maleic acid), polycarbonates, polyalkylenes, polyalkylene terephthalates, polyvinyl alcohols, polyvinyl ethers, polyvinyl esters, polyvinyl halides, polysiloxanes, polystyrene, poly (lactide-co-glycolide), blends and copolymers thereof.

Another aspect of the invention relates to a method of treating an individual (human, non-human primate, non-human mammal, rodents, livestock animals, birds, vertebrates, insects, worms, etc.) for a disease condition associated with a phagocytic cell defect, such as a macrophage defect, comprising administering to the individual any of the subject delivery system, wherein the RNAi construct antagonizes the function of a target gene causing the disease condition.

Examples of genes that can be targeted using the present method include, but are not limited to genes associated with inflammatory disorders, such as MAP4K4,TNF-α, IL1-α, IL1β, IL-12,IL-6,IL-23,NFκB pathway genes (including any of the subunits and up-stream or downstream genes in the NFκB pathway), subgroups of c-Jun N-terminal kinase (e.g., JNK1,JNK2,JNK3), NRAMP-1,JAK2 and IRAK4.Additionally, genes associated with tolerance induction and autoimmunity include, for example, CD40,CD80, CD86,OX4OL, and IFNR type 1.Furthermore, disease associated with metabolism and diabetes (e.g., Type I Diabetes) can also be treated by targeting, for example, aP2/FABP4 and RIP140.In this aspect, the present delivery system can be used to target a gene(s) for the treatment of a wide range of disorders related to inflammation and tolerance induction as well as autoimmune and metabolic conditions.

Exemplary non-limiting disorders that can be treated using the present method include: arthritis (such as rheumatoid arthritis, psoriatic arthritis or osteoarthritis); transplant (such as organ transplant, acute transplant or heterograft or homograft (such as is employed in burn treatment)) rejection; protection from ischemic or reperfusion injury such as ischemic or reperfusion injury incurred during organ transplantation; transplantation tolerance induction; psoriasis; multiple sclerosis; inflammatory bowel disease, including ulcerative colitis and Crohn's disease; acute inflammatory responses (such as acute respiratory distress syndrome and ishchemia/reperfusion injury); allergic diseases such as respiratory allergies (asthma, hayfever, allergic rhinitis); lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; Hashimoto's thyroiditis; Sjogren's syndrome; autoimmune Hyperthyroidism, such as Graves' Disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituitarism; Guillain-Barre syndrome; other autoimmune diseases; inhibition of T cell activation and proliferation; systemic sclerosis; and morphea. In addition, metabolic disorders such as Type II diabetes, metabolic syndrome, as well as related disorders such as, hypertension, coronary heart disease, hypercholesterolemia, dyslipidemia, gallstones, or liver fibrosis can also be the subject of the present methods.

In certain embodiments, the target gene is overexpressed in the individual.

The subject methods encompass the recognition that phenotype(s) of phagocytic cells such as macrophages and related cells can be modified, and provide compositions and methods for achieving such modification(s) for the treatment and/or prevention of a variety of diseases and conditions. These diseases and conditions include, but are not limited to, macular degeneration, osteoporosis, immune inflammation (including arthritis, asthma, Crohn's disease, inflammatory bowel disease, type I diabetes, type II diabetes, multiple sclerosis, artherosclerosis), non-immune inflammation, tuberculosis, multiple sclerosis, chronic obstructive pulmonary disease (COPD) and Alzheimer's disease. Further, methods for treating disease states associated with activation of innate immune system signaling are provided in accordance with other aspects of the present invention. Diseases may be, for example, sepsis and septic shock, neurodegeneration, neutrophilic alveolitis, asthma, hepatitis, inflammatory bowel disease, ischemia/reperfusion, septic shock, glomerulonephritis, rheumatoid arthritis or Crohn's disease.

Another aspect of the invention provides a pharmaceutical composition, preferably suitable for oral delivery or injection, of an RNAi construct to a phagocytic cell such as a macrophage, comprising any of the subject delivery system, and pharmaceutically acceptable excipients for oral delivery or injection.

In a related aspect, the invention further provides a pharmaceutical package comprising the subject pharmaceutical preparation, in association with instructions (written or pictorial) for administering the preparation to an individual, such as a human patient.

The subject RNAi constructs may additionally contain various structural features, modifications, size limitations, etc., to enhance serum stability, target specificity, and various other benefits. The detailed descriptions of these features and other features of the invention are provided in the sections below.

2.RNAi Conjugates

The subject RNAi constructs may be conjugated to a nanotransporter, a nanoparticle, PEI, a carrier RNA core, or in general a payload trapping molecule, for more efficient delivery into the target cell (e.g., phagocytic cells such as macrophages or macrophage-like cells). The conjugate preferably also contain pharmaceutically acceptable excipient for in vivo use. The nanotransporter, nanoparticle, PEI, carrier RNA core or the payload trapping molecule are preferably water soluble and/or biodegradable. They selectively binds to and confines the RNAi constructs, providing an affinity interaction that contributes to the retention of the RNAi constructs.

i) Payload Trapping Molecule, such as PEI

In general, polyelectrolytes can be suitable payload trapping molecules. Several suitable polyelectrolytes are disclosed in U.S. Pat. No. 6,133,229.The polyelectrolyte may be a cationic or anionic polyelectrolyte. Amphoteric polyelectrolytes may also be employed. The cationic polyelectrolyte is preferably a polymer with cationic groups distributed along the molecular chain. The cationic groups, which in certain embodiments may include quaternary ammonium- derived moieties, may be disposed in side groups pendant from the chain or may be incorporated in it. Examples of cationic polyelectrolytes include: copolymers of vinyl pyrollidone and quaternary methyl methacrylate, e.g., GAFQUAT®, series (755N, 734,HS-100) obtained from ISP; substituted polyacrylamides; polyethyleneimine (PEI), polypropyleneimine and substituted derivatives; polyamine homopolymers (GOLCHEM® CLI 18); polyamine co-polymers (e.g., condensates of epichlorohydrin and mono or dimethylamine); polydiallyl dimethyl ammonium chloride (polyD ADMAC); substituted dextrans; modified guar gum (substituted with hydroxypropytrimonium chloride); substituted proteins (e.g., quaternary groups substituted on soya protein and hydrolysed collagen); polyamino acids (e.g., polylysine); low molecular weight polyamino compounds (e.g., spermine and spermidine). Natural or artificial polymers maybe employed. Cationic polyelectrolytes with MW 150 to 5,000,000,preferably 5000 to 500,000,more preferably 5000 to 100,000 maybe employed. An amount of 0.01 to 10% is preferred, more preferably 0.1 to 2% w/v, especially 0.05 to 5%.

The anionic polyelectrolyte is preferably a polymer with anionic groups distributed along the molecular chain. The anionic groups, which may include carboxylate, sulfonate, sulphate or other negatively charged ionisable groupings, may be disposed upon groups pendant from the chain or bonded directly to the polymer backbone. Natural or artificial polymers may be employed.

Examples of anionic polyelectrolytes include: a copolymer of methyl vinyl ether and maleic anhydride, a copolymer of methyl vinyl ether and maleic acid, (Gantrez AN-series and S-series, respectively, International Specialty Products, Wayne, N.J.); alginic acid and salts; carboxymethyl celluloses and salts; substituted polyacrylamides (e.g., substituted with carboxylic acid groups); polyacrylic acids and salts; polystyrene sulfonic acids and salts; dextran sulphates; substituted saccharides e.g., sucrose octosulfate; heparin. Anionic polyelectrolytes with MW of 150 to 5,000,000 maybe used, preferably 5000 to 500,000,more preferably 5000 to 100,000.An amount of 0.01% to 10% is preferred especially 0.05 to 5% more especially 0.1 to 2% w/v.

Biological polymers, such as polysaccharides, are preferred trapping polymers. Preferably, the polymers are processed to an average molecular weight to less than 100,000 Daltons. The polymers are preferably derivatized to provide cationic or anionic characteristics. Suitable polysaccharides include chitosan (deacetylated chitin), alginates, dextrans, such as 2-(diethylamino) ethyl ether dextran (DEAE-dextran) and dextran sulphate, xanthans, locust bean gums and guar gums.

Two general classes of cationic molecules are suitable for use as trapping molecules with negatively charged payloads such as polynucleotides: cationic polymers and cationic lipids.

A wide variety of cationic polymers have been shown to mediate in vitro transfection, ranging from proteins [such as histones (Fritz, J. D., et al, (1996) Hum. Gene Ther. 7, 1395-1404) and high mobility group (HMG) proteins (Mistry, A. R., et al. (1997) BioTechniques 22. 718-729) and polypeptides [such as polylysine (Wu, G. Y. & Wu, C. H. (1987) J. Biol. Chem. 262, 4429-4432,Wagner, E., et al., (1991) Bioconjugate Chem. 2, 226-231,short synthetic peptides (Gottschalk et al., (1996) Gene Ther. 3, 448-457; Wadhwa, M. S., et al., (1997) Bioconjugate Chem. 8, 81-88), and helical amphophilic peptides (Legendre, J. Y., et al, (1997) Bioconjugate Chem. 8, 57-63; Wyman, T. B., et al., (1997) Biochemistry 36, 3008-3017)] to synthetic polymers [such as polyethyleneimine (Boussif, 0.,et al., (1996) Gene Ther. 3, 1074-1080), cationic dendrimers (Tang, M. X., et al., (1996) Bioconjugate Chem. 7, 703-714; Haensler, J. et al., (1993) Bioconjugate Chem. 4, 372-379), and glucaramide polymers (Goldman, C. K., et al., (1997) Nat. Biotech. 15, 462-466)]. Other suitable cationic polymers include N-substituted glycine oligomers (peptoids) (Murphy, J.E., et al, A combinatorial approach to the discovery of efficient cationic peptoid reagents for gene delivery, Proc Natl Acad Sci. USA, 1998 95 (4)1517-1522), poly(2-methyl-acrylic acid 2-[(2-dimethylamino)-ethyl)-methyl-amino]-ethyl ester), abbreviated as pDAMA, and poly(2-dimethylamino ethyl)-methacrylate (pDMAEMA) (Funhoff, A. M., et al., 2004 Biomacromolecules, 5, 32-39).

Cationic lipids are also known in the art to be suitable for transfection. Feigner et al., Lipofection: a highly efficient, lipid-mediated DNA-transfection procedure. Proc Natl Acad Sci U S A. 1987 84(21):7413-7.Suitable cationic lipids include N-[1-(2,3-dioleyloxy)propyl]-N,N,N-trimethylammonium chloride (DOTMA), [N5N5N', N'-tetramethyl-N,N'-bis(2-hydroxyethyl) -2,3-di(oleyloxy)-1,4-butanediammonium iodide] (Promega Madison, Wis., USA), dioctadecylamidoglycyl spermine (Promega Madison, W15 USA), N-[1-(2,3-Dioleyloxy)]-N5N, N-trimethylammonium propane methylsulfate (DOTAP), N-[1-(2,3-dioleyloxy)propyl]-N5N,N-trimethylammonium chloride, 1,2-dimyristyloxypropyl-3-dimethyl-hydroxy ethyl ammonium bromide (DMRIE)5 dimyristoleoyl phosphonomethyl trimethyl ammonium (DMPTA) (see Floch et al. 1997.Cationic phosphonolipids as non-viral vectors for DNA transfection in hematopoietic cell lines and CD34+ cells. Blood Cells, Molec. & Diseases 23: 69-87), 1,2-dioleoyl-sn-glycero-3-phosphoethanolamine-N-(7-nitro-2-1,3-benzoxadiazol-4-yl), ammonium salt (Avanti Polar Lipids, Inc. Alabaster, Ala., US)5 1,2-dioleoyl-3-trimethylammonium-propane chloride (Avanti Polar Lipids, Inc. Alabaster, Ala., US)5 1,2- dioleoyl-sn-glycero-3-phosphoethanolamine (Avanti Polar Lipids, Inc. Alabaster, Ala., US) and 1 ,3-dioleoyloxy-2-(6-carboxyspermyl)propylamide (DOSPER). Polyamines suitable as cationic trapping molecules are described in U.S. Pat. Nos. 6,379,965 and 6,372,499.

ii) Shaped Nanoparticle

In another embodiment of the invention, the subject RNAi constructs may be conjugated to payload trapping molecules and molded into a non-disperse particles, such as one manufactured based on the PRINT™ (Particle Replication in Non-Wetting Templates) technology as described by Liquidia Technologies, Inc. (Research Triangle Park, N.C.). Specifically, such particles can be manufactured to have sizes ranging from about 10 nm to about 500 µm. In addition to their wide particle size range, the PRINT™ particles may vary in shape profiles. Unlike previous techniques, which have produced "polydisperse" particle mixtures with sizes ranging from hundreds of nanometers to tens of microns, the PRINT™ process forms particles of uniform size and shape. With such predetermined uniform size and shape profile, drug stability, solubility, and concentration may be optimized, and interparticle forces that cause aggregation is minimized.

Thus in one embodiment, the subject RNAi constructs (optionally with one or more payload trapping molecules) may be molded to have a size and shape of a bacterium, such as a rod or bead shape with a length or diameter of about 100 nm to about 20 micron, or about 500 nm to about 5 micron. Optionally, the shaped nanoparticles may be further coated with one or more phagocytic cell-targeting moieties to facilitate more specific delivery to phagocytic cells such as macrophages or macrophage-like cells.

In general, the PRINT™ particles may be formed from a large variety of matrix compositions (e.g., organic polymers, organic and inorganic materials, active pharmaceutical ingredients and biologics) with the ability to carry a large therapeutic payload. Thus any of the payload trapping molecules described herein may be used to generate the subject shaped nanoparticles. The PRINT™ surface can be tailored to suit the needs of the system by varying the surface with targeting ligands and/or surface charge, for example. Additionally, the PRINT™ system may be designed to respond to biological and environmental changes such as pH, temperature, and presence of specific enzymes for varied triggered release of the therapeutic compound. The PRINT™ platform offers improved safety, efficacy, and/or dosing requirements by providing reduced off-target effects, minimal systemic exposure, and the ability to concentrate drug particles at the intended site of action. The PRINT™ platform also has improved drug efficacy and reduced dosing requirements, improved solubility, enhanced dissolution rates, and improved ability to cross biological barriers (e.g., blood brain barrier, cell membranes, extracellular matrices).

iii) Nanotransporters

The siRNAs of the invention can also be delivered by the use of nanotransporters. In certain embodiments, nanotransporters comprise a core that includes a nanoparticle or a "nanotube," and at least one functional surface group as described herein. The functional surface groups are chosen for their ability to increase the functionality of the nanotransporter, such as enhanced cell-targeting specificity.

The term "nanotransporter" refers to a multi-component complex with controlled dimensions, e.g., a diameter or radius on the order of about 1 to about 1000 nanometers. In one embodiment, the nanotransporter is about 1 to about 100 nanometers in diameter. In another embodiment, the nanotransporter is about 1 to about 75 nanometers in diameter. In another embodiment, the nanotransporter is about 10, 20, 30, 40, 50, 60, 70, 80, 90,or 100 nanometers in diameter. In one embodiment, the nanotransporters comprise about 1 to about 50 functional surface groups. In another embodiment, the nanotransporters comprise about 1 to about 25 functional surface groups. In another embodiment, the nanotransporters comprise about 1 to about 10 functional surface groups (e.g., 1, 2, 3, 4, 5, 6, 7, 8 9,or 10 functional surface groups). In certain embodiments, the functional surface groups are the same. In other embodiments, different combinations of functional surface groups are used (e.g., 2, 3, 4, 5,or 6 types of functional surface groups are used).

In some embodiments, the nanoparticle, as referred to above, is a dendrimer or a polylysine dendrimer. Dendrimers are highly branched polymers with well-defined architecture, capable of delivery other compounds into a cell. Three non-limiting examples of dendrimers are taught by Rana, T. M. in WO/2007/089607,which is incorporated herein by reference in its entirety.

In an exemplary embodiment, the NOP-7 nanotransporter is combined with the subject RNAi constructs to form a delivery complex termed "iNOP-y." The NOP-7 nanotransporter (see FIG. 26 in WO/2007/089607,incorporated herein by reference) is a generation-4 lysine dendrimer, which was chemically synthesized, labeled with oleoyl lipids, purified and characterized by NMR and mass spectrometry (see FIGS. 27 and 28 of WO/2007/089607,incorporated herein by reference). Dynamic light scattering experiments showed that the average diameter of NOP-7 was about 15 nm (FIG. 29A of WO/2007/089607).

Exemplary iNOP7 delivery complexes can be prepared by mixing the RNAi constructs and the NOP-7 nanotransporter at a ratio of 1:2 (w/w) in Hepes saline or Opti-MEM culture medium (Invitrogen), and incubating at room temperature for about 20 min.

Many dendrimers are commercially available, e.g., from Sigma-Aldrich. The dendrimers of the invention include but are not limited to the following: PAMAM: Amine terminated and/or PAMAM: Carboxylic Acid terminated (available, e.g., from Dendritech, Inc., Midland, Mich.); Diaminobutane (DAB)-DAB: Amine terminated and/or DAB: Carboxylic Acid terminated; PEGs: OH terminated (Frechet et al. JACS 123:5908 (2001)), among others. In general, PAMAM or a variant thereof is used.

In another aspect, the "nanotube" that forms the core is a hollow cylindrical structure with an outside diameter of about 1 to about 5 nanometers. Exemplary nanotubes are carbon nanotubes. In certain embodiments, the nanotube is a single-walled nanotube, i.e., a single tube, that is about 1 nanometer in diameter and about 1 to about 100 microns in length. In other embodiments, the nanotube is a multi-walled nanotube, i.e., a tube with at least one other tube embedded within it. In some embodiments, nanotubes can have one end capped with the hemisphere of a fullerene-like structure. Nanotube-siRNA conjugates can be formed according to the method described in WO/2007/089607.

In another embodiment, the functional surface group can further include, in addition to a cell targeting moiety as described herein, a charge controlling molecule. A "charge controlling molecule," as used herein, refers to a molecule which contributes to the overall ionic environment or net charge of a nanotransporter. In one embodiment, the addition of a charge controlling molecule facilitates the association between the nanotransporter and a siRNA molecule and the formation of a delivery complex. In another embodiment, the addition of a charge controlling molecule facilitates improved cellular uptake of the delivery complex into the cell. Exemplary charge controlling molecules and methods of using such molecules with a nanotransporter can be found in WO/2007/089607.In certain embodiments, the charge controlling molecules are the same chemical structure or class. It is further recognized that any combination of lipids may be employed together with any combination of charge controlling molecules.

The nanotransporters might be formed within the beta-glucan shells, or may be used alone (without being attached to the beta-glucan shells).

3.Phagocytic cell-Targeting Moieties

Various phagocytic cell-targeting moieties can be used in the delivery system of the invention.

In certain embodiments, the phagocytic cell-targeting moiety comprises beta-glucan, which can be recognized by receptors on phagocytic cells, such as macrophages and other macrophage-like cells, as well as on cells of lymphoid tissue. The mucosal-associated lymphoid tissue (MALT) comprises all lymphoid cells in epithelia and in the lamina propria lying below the body's mucosal surfaces. The main sites of mucosal-associated lymphoid tissues are the gut-associated lymphoid tissues (GALT), and the bronchial-associated lymphoid tissues (BALT).

Another important component of the GI immune system is the M or micro fold cell. M cells are a specific macrophage-like cell type in the intestinal epithelium over lymphoid follicles that endocytose a variety of protein and peptide antigens. Instead of digesting these proteins, M cells transport them into the underlying tissue, where they are taken up by local dendritic cells and macrophages.

M cells take up molecules and particles from the gut lumen by endocytosis or phagocytosis. This material is then transported through the interior of the cell in vesicles to the basal cell membrane, where it is released into the extracellular space. This process is known as transcytosis. At their basal surface, the cell membrane of M cells is extensively folded around underlying lymphocytes and antigen-presenting cells, which take up the transported material released from the M cells and process it for antigen presentation.

A study has shown that transcytosis of yeast particles (3.4+/−0.8 micron in diameter) by M cells of the Peyer's patches takes less than 1 hour (Beier, R., & Gebert, A., Kinetics of particle uptake in the domes of Peyer's patches, Am J Physiol. 1998 Jul; 275(1 Pt 1):G130-7). Without significant phagocytosis by intraepithelial macrophages, the yeast particles migrate down to and across the basal lamina within 2.5-4 hours, where they quickly get phagocytosed and transported out of the Peyer's patch domes. M cells found in human nasopharyngeal lymphoid tissue (tonsils and adenoids) have been shown to be involved in the sampling of viruses that cause respiratory infections. Studies of an in vitro M cell model have shown uptake of fluorescently labeled microspheres (Fluospheres, 0.2 μm) and chitosan microparticles (0.2 μm) van der Lubben I. M., et al., Transport of chitosan microparticles for mucosal vaccine delivery in a human intestinal M- cell model, *J Drug Target,* 2002 September; 10(6):449-456.A lectin, Ulex europaeus agglutinin 1 (UEA1,specific for alpha-L-fucose residues) has been used to target either polystyrene microspheres (0.5 µm) or polymerized liposomes to M cells (0.2 µm) (Clark, M. A., et al., Targeting polymerised liposome vaccine carriers to intestinal M cells, Vaccine. 2001 Oct. 12; 20(1-2):208-17). In vivo studies in mice have reported that poly-D,L-lactic acid (PDLLA) microspheres or gelatin microspheres (GM) can be efficiently taken up by macrophages and M cells (Nakase, H., et al., Biodegradable microspheres targeting mucosal immune-regulating cells: new approach for treatment of inflammatory bowel disease, J Gastroenterol. 2003 March; 38 Suppl 15:59-62).

Uptake of such synthetic particulate delivery vehicles including poly(DL-lactide-co-glycolide) microparticles and liposomes is to some extent determined by the physical properties of both particles and M cells. Clark, M. A., et al., Exploiting M cells for drug and vaccine delivery, Adv Drug Deliv Rev. 2001 Aug. 23; 50(1-2):81-106.Delivery may be enhanced by coating the particles or liposomes with reagents including appropriate lectins, microbial adhesins and immunoglobulins which selectively bind to M cell surfaces. See also, Florence, A. T., The oral absorption of micro- and nano-particulates: neither exceptional nor unusual, Pharm Res. 1997 Mar;14(3):259-66.

In certain embodiments, liposomes or cationic lipids may be used as delivery vehicle in the subject delivery system. For example, liposomes or cationic lipids may encapsulate the subject RNAi constructs with or without the payload trapping molecules, and formulated for oral delivery or injection. Preferably, the subject macrophage/M cell targeting moiety is covalently linked to the lipid used to form the liposome. This lipid-macrophage/M cell targeting moiety conjugate can be used as 0.5%, 1%, 2%, 5%, 10%, 20%, 30%, 40%, 50%, 60%, 70%, 80%, 90%, or 100% of the total lipids for making the liposome or cationic lipid particles. The other lipids in the liposome or cationic lipid particle may be identical or similar to the lipid in the conjugate, but do not have macrophage/M cell targeting moiety.

One exemplary liposome suitable for the instant invention (e.g., oral administration or injection) is amphoteric liposome, which simultaneously comprises positive and negative membrane-based or membrane-forming charge carriers. See, for example, U.S. Pat. No. 7,371,404 and EP 1363601 (both incorporated by reference). In one embodiment, the amphoteric liposome comprises an active ingredient (e.g., the subject RNAi construct), has an isoelectric point of between 4 and 7,wherein the liposome comprises at least one amphipatic cationic lipid, at least one amphipatic anionic lipid, and at least about 30% neutral lipid, and wherein the liposome is stable at pH 4.2 and p1-I 7.5,or an isoelectric point of between 5 and 7.In another embodiment, the amphoteric liposome comprises an active ingredient (e.g., the subject RNAi construct), wherein the liposome comprises at least one amphipatic lipid with both a positive charge and a negative charge, and at least about 30% neutral lipid, wherein the amphoteric liposome has an isoelectric point of between 4 and 8 and are stable at pH 4.2 and pH 7.5.The liposome may further comprise at least one amphipatic lipid with a positive charge or at least one amphipatic lipid with a negative charge. The neutral lipid may be selected from the group consisting of phosphatidyl choline, phosphatidyl ethanolamine, cholesterol, tetra-ether lipid, ceramide, sphingolipid, and diacyl glycerol. The anionic lipid may be a weak anion and the cationic lipid may be a strong cation and the anion may be present in excess over the cation. The weakly anionic lipid may be selected from the group consisting of cholesterol hemisuccinate (CHEMS), diacyl glycerol hemisuccinate, fatty acids and phosphatidyl serine. The strongly cationic lipid may be selected from the group consisting of DOTAP, DC-Chol, DORIE, DDAB, TC-Chol, DOTMA, DOGS, $(C18)_2Gly^+$ N,N-dioctadecylamido-glycin, CTAB, CPyC and DOEPC. The anionic lipid may be CHEMS or diacylglycerol hemisuccinate, the cationic lipid may be DOTAP or DC-Chol and the neutral lipid may be phosphatidylcholine.

Exemplary liposomes may comprise about 50 mol. % POPC, about 20 mol. % DOTAP and about 30 mol. % CHEMS; about 50 mol. % POPC, about 10 mol. % DOTAP and about 40 mol. % CHEMS; about 60 mol. % POPC, about 10 mol. % DOTAP and about 30 mol. % CHEMS; about 60 mol. % POPC, about 15 mol. % DOTAP and about 25 mol. % CHEMS; about 30 mol. % POPC, about 30 mol. % DOTAP and about 40 mol. % CHEMS; about 60 mol. % POPC, about 15 mol. % DC-Chol and about 25 mol. % CHEMS.

In certain embodiments, the anionic lipid is a weak anion and the cationic lipid is a weak cation. The weakly anionic lipid may be selected from the group consisting of cholesteryl hemisuccinate (CHEMS), diacyl glycerol hemisuccinate, fatty acids and phosphatidyl serine. The weakly cationic lipid may be selected from the group consisting of HisChol and MoChol. Preferably, the weakly anionic lipid is CHEMS or diacylglycerol hemisuccinate, and the weakly cationic lipid is HisCRol or MoChol and the neutral lipid is phosphatidylcholine. The liposome may comprise about 55 mol. % POPC, about 40 mol. % HisChol and about 5 mol. % CHEMS; or comprises about 60 mol. % POPC, about 20 mol. % HisChol and about 20 mol. % CHEMS.

In certain embodiments, the anionic lipid is a strong anion and the cationic lipid is a weak cation and the cation is present in excess over the anion. The strongly anionic lipid may be selected from the group consisting of cholesterol sulphate, cholesterol phosphate, phosphatidyl glycerol, phosphatidic acid, phosphatidyl inositol, cetyl phosphate. The weakly cationic lipid is selected from the group consisting of HisChol and MoChol. Preferably, the strongly anionic lipid is selected from phosphatidylglycerol, phosphatidic acid, or cetyl phosphate and the weakly cationic lipid is selected from HisChol or MoChol and the neutral lipid is phosphatidylcholine. The liposome comprises about 47.5 mol. % POPC, about 40 mol. % HisChol and about 12.5 mol. % DPPG.

The liposome may have an average size of between 50 and 1000 nm, or between 70 and 250 nm, or between 60 and 130 nm. At least 80% of the active ingredient may be in the interior of the liposome.

Another exemplary lipid-based formulations for delivering nucleic acids to a cell is "SNALP," which refers to a Stable Nucleic Acid Lipid Particle, including SPLP (stabilized nucleic acid-lipid particles). A SNALP represents a vesicle of lipids coating a reduced aqueous interior comprising a nucleic acid (e.g., any of the subject RNAi constructs, including siRNA, and plasmid, including plasmid from which an interfering RNA is transcribed). As used herein, the term "SPLP" refers to a nucleic acid lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs have systemic application as they exhibit extended circulation lifetimes following intravenous (i.v.) injection, accumulate at distal sites (e.g., sites physically separated from the administration site and can mediate expression of the transfected gene at these distal sites. SPLPs include "pSPLP," which comprise an encapsulated condensing agent-nucleic acid complex as set forth in WO 00/03683.

SNALPs and SPLPs are described in U.S. 2005-0175682 A1,U.S. 2003-0077829 A1, and US 2005-0064595 A1 (all incorporated by reference).

For example, U.S. 2003-0077829 A1 describes stabilized nucleic acid-lipid particles (SPLPs) and other lipid-based carrier systems containing polyethyleneglycol (PEG)-diacylglycerol (DAG) conjugates, i.e., PEG-DAG conjugates or alternatively DAG-PEG conjugates. In a preferred embodiment, the SPLPs contain a cationic lipid (e.g., DOTMA) a non-cationic lipid (e.g., DSPC), and a PEG-DAG conjugate (e.g. PEG-dilaurylglycerol). Examples of cationic lipids include, but are not limited to, DODAC, DODAP, DODMA, DOTAP, DOTMA, DC-Chol, DMRIE, DSDAC, and DDAB. Suitable non-cationic lipids include, but are not limited to, DSPC, DOPE, DOPC, EPC, cholesterol, and mixtures thereof. Examples of DAG-PEG conjugates include, but are not limited to, a PEG-dilaurylglycerol conjugate (C12), a PEG- dimyristylglycerol (C14) conjugate, a PEG-dipalmitoylglycerol (C16) conjugate and a PEG-disterylglycerol (C18) conjugate. Such SPLPs can used to deliver any of a variety of the subject RNAi constructs. The SPLPs of the present invention typically have a mean diameter of less than about 150 nm and are substantially nontoxic. In addition, the nucleic acids when present in the SPLPs of the present invention are resistant to aqueous solution to degradation with a nuclease. SPLPs and their method of preparation are disclosed in U.S. Pat. Nos. 5,976,567, 5,981,501 and PCT Patent Publication No. WO 96/40964,the teachings of all of which are incorporated herein by reference.

Specifically, the application describes a nucleic acid-lipid particle comprising: a nucleic acid; a cationic lipid; a non-cationic lipid; and a polyethyleneglycol-diacylglycerol (PEG-DAG) conjugate. The cationic lipid may be a member selected from the group consisting of N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), and N,N-dimethyl-2,3-dioleyloxy)propylamine (DODMA), and a mixture thereof The non-cationic lipid may be a member selected from the group consisting of dioleoylphosphatidylethanolamine (DOPE), palm itoyloleoylphosphatidylcholi-ne (POPC), egg phosphatidylcholine (EPC), distearoylphosphatidylcholine (DSPC), cholesterol, and a mixture thereof The PEG-DAG conjugate may be a member selected from the group consisting of PEG-dilaurylglycerol (C12), a PEG-dimyristylglycerol (C 14), a PEG-dipalmitoylglycerol (C 16), and a PEG-disterylglycerol (C18). The cationic lipid comprises from about 2% to about 60% of the total lipid present in the particle, or from about 5% to about 45% of the total lipid present in the particle, or from about 5% to about 15% of the total lipid present in the particle, or from about 40% to about 50% of the total lipid present in the particle. The non-cationic lipid comprises from about 5% to about 90% of the total lipid present in the particle, or from about 20% to about 85% of the total lipid present in the particle. The PEG-DAG conjugate comprises from 1% to about 20% of the total lipid present in the particle, or from about 4% to about 15% of the total lipid present in the particle.

A preferred non-cationic lipid is DSPC. The liposome may further comprise cholesterol. For example, the cholesterol may comprise from about 10% to about 60% (or from about 20% to about 45%) of the total lipid present in the particle.

In certain embodiments, the cationic lipid comprises 7.5% of the total lipid present in the particle; the non-cationic lipid comprises 82.5% of the total lipid present in the particle; and the PEG-DAG conjugate (such as PEG-dilaurylglycerol (C12), PEG-dimyristylglycerol (C14), PEG-dipalmitoylglycerol (C16), or PEG-disterylglycerol (C18)) comprises 10% of the total lipid present in the particle. In certain embodiments, the nucleic acid-lipid particle further comprises cholesterol.

In certain embodiments, the nucleic acid-lipid particle comprises: DODMA; DSPC; and a PEG-DAG conjugate.

In certain embodiments, the subject RNAi constructs are fully encapsulated in the nucleic acid-lipid particle.

U.S. 2005-0175682 A1 provides novel polyethyleneglycol-dialkyloxyp-ropl (PEG-DAA) conjugates that have increased stability over commonly used PEG-lipid conjugates (such as PEG-PE conjugates). The PEG-modified dialkylpropyl conjugates described therein enhance the properties of liposomes as well as nucleic acid-lipid particles (e.g., SNALPs and SPLPs) by increasing the circulation longevity or lifetime of the liposome, SNALP, or SPLP. In fact, it has been found that the PEG-DAA conjugates are more stable than other commonly used PEG-lipid derivatives. As a result of their increased stability, the PEG-DAA conjugates increase the circulation longevity or lifetime of the liposome or SPLP and also reduce leakage due to hydrolysis of the fatty acyl chains of the liposome bilayer or the SPLP when other PEG-lipid conjugates are used.

One source for beta-glucan is extracted yeast cell wall particles, which can be readily made using art-recognized methods. These particles are about 2-4 µm in diameter, and are biodegradable and substantially spherical. Preparation of extracted yeast cell wall particles is known in the art, and is described, for example in U.S. Pat. Nos. 4,992,540, 5,082, 936, 5,028,703, 5,032,401, 5,322,841, 5,401,727, 5,504,079, 5,968,811, 6,444,448 B1, 6,476,003 B1,published U.S. applications 2003/0216346 A1, 2004/0014715 A1,and PCT published application WO 02/12348 A2 (all incorporated herein by reference). A form of extracted yeast cell wall particles, referred to as "whole glucan particles," is described in U.S. Pat. Nos. 5,032,401 and 5,607,677 (all incorporated herein by reference).

Alternatively, beta-glucan can be synthesized using any art-recognized methods. Synthesized beta-glucan may be conjugated to certain macromolecules or polymers, such as cyclodextran (CD) polymers, to provide relatively ordered synthetic beta-glucan particles.

In certain embodiments, the phagocytic cell-targeting moiety is a ligand recognized by pathogen pattern recognition receptors (PRRs), which recognize common structural and molecular motifs present on microbial surfaces and contribute to induction of innate immune responses. Mannose receptors and beta-glucan receptors in part participate in the recognition of fungal pathogens. The mannose receptor (MR), a carbohydrate-binding receptor expressed on subsets of macrophages, is considered one such PRR. Macrophages have receptors for both mannose and mannose-6-phosphate that can bind to and internalize molecules displaying these sugars. The molecules are internalized by endocytosis into a pre-lysosomal endosome. This internalization has been used to enhance entry of oligonucleotides into macrophages using BSA modified with mannose-6-phosphate and linked to an oligodeoxynucleotide by a disulfide bridge to a modified 3' end; see Bonfils, E., et al., Nucl. Acids Res. 1992 20, 4621-4629.see E. Bonfils, C. Mendes, A. C. Roche, M. Monsigny and P. Midoux, Bioconj. Chem., 3, 277-284 (1992). Macrophages also express beta-glucan receptors, including CR3 (Ross, G. D., J. A. Cain, B X. Myones, S. L. Newman, and P J. Lachmann. 1987.Specificity of membrane complement receptor type three (CR3) for f3-glucans. Complement Inflamm. 4:61), dectin-1.(Brown, G. D. and S. Gordon. 2001. Immune recognition. A new receptor for 13-glucans. Nature 413:36), and lactosylceramide (Zimmerman J W, Lindermuth J, Fish P A, Palace G P, Stevenson T T, DeMong D E. A novel carbohydrate-glycosphinglipid interaction between a beta-(1-3)-glucan immunomodulator, PGG-glucan, and lactosylceramide of human leukocytes. J Biol Chem. 1998 Aug. 21:273(34):22014-20). The beta-glucan receptor, CR3 is predominantly expressed on monocytes, neutrophils and NK cells, whereas dectin-1 is predominantly expressed on the surface of cells of the macrophages. Lactosylceramide is found at high levels in M cells. Microglia can also express a beta-glucan receptor (Muller, C D., et al. Functional beta-glucan receptor expression by a microglial cell line, Res Immunol. 1994 May; 145(4):267-75).

There is evidence for additive effects on phagocytosis of binding to both mannose and beta-glucan receptors. Giaimis et al. reported observations suggesting that phagocytosis of unopsonized heat-killed yeast (*S. cerevisiae*) by murine macrophage-like cell lines as well as murine peritoneal resident macrophages is mediated by both mannose and beta-glucan receptors. To achieve maximal phagocytosis of unopsonized heat-killed yeast, coexpression of both mannose and beta-glucan receptors is required (Giaimis, J., et al., Both mannose and beta-glucan receptors are involved in phagocytosis of unopsonized, heat-killed Saccharomyces cerevisiae by murine macrophages, J Leukoc Biol. 1993 December; 54(6): 564-71).

Other endocytic pattern recognition receptor may include, for example, mannose receptors, scavenger receptors, opsonin receptors, and N-formyl Met receptors. Examples of scavenger receptors include MARCO, CD36,CD86,and SRB-1.Examples of opsonin receptors include gp-340,CR1,and CR3.Additionally, the targeting moiety or ligand will be recognized and bound by a pattern recognition receptor molecule of the innate immunity system that elicits a cellular or humoral immune response in a mammal. The ligand may be selected for recognition by Toll-like receptors. The Toll-like receptors can include, but are not limited to, TLR-1,TLR-2, TLR-3,TLR-4,TLR-5,TLR-6,TLR-7,TLR-8,TLR-9, TLR-10,TLR-11,and TLR-12 or combinations thereof. Examples of TLR ligands can include, but are not limited to, gram+ bacteria (TLR-2), bacterial endotoxin TLR-4), flagellin protein (TLR-5), bacterial DNA (TLR-9), double-stranded RNA and poly (TLR-3), and yeast cell wall antigens (TLR-2).

Accordingly, the present invention may utilize any pattern recognition receptor ligand. The ligands may be glycoproteins, lipoproteins, glycolipids, carbohydrates, lipids, and/or protein or peptide sequences derived from any portion of a fungal, viral, rickettsial, parasitic, arthropod or bacterial organism. In another embodiment, the active agent may comprise multiple ligands.

In yet another embodiment, the phagocytic cell-targeting moiety may be an antibody (such as a monoclonal antibody or any of the art-recognized functional fragments thereof, including scFv, $F(ab)_2$, etc.) that binds one or more proteins/receptors on the surface of a phagocytic cell such as a macrophage. A few representative art-recognized macrophage surface markers are briefly described below. Other art-recognized or known phagocytic cell markers, such as macrophage surface markers, may also be used for specific targeting using antibody-based macrophage-targeting moiety. Antibodies or functional fragments thereof specific for such phagocytic cell markers, such as macrophage markers, as well as ligands for these phagocytic cell markers, such as macrophage markers, can be used as the subject phagocytic cell-targeting moieties. In certain embodiments, the markers are restricted to specific subsets of phagocytic cells, such as subsets of macrophages, and the macrophage-targeting moiety may be used to specifically targeting the specific subset of macrophages.

The complete EGF-TM7 family proteins comprise human and mouse CD97,mouse F4/80,human EMR1 (EGF-module-containing mucin-like hormone receptor 1), human EMR2, EMR3 mEMR4,and ETL. These predominantly leukocyte-restricted glycoproteins are defined by their unique chimaeric structures which consist of varying numbers of N-terminal epidermal growth factor (EGF)-like repeats coupled to a family B G-protein coupled receptor (GPCR)-related moiety via a mucin-like spacer region. Human/mouse CD97 and EMR1-4 have identified homologs in cows, pigs and zebrafish.

As a result of its macrophage-restricted expression, F4/80 has long been used as an excellent marker for populations of mouse tissue macrophages. F4/80 is restricted to many, but not all mature macrophages. It is an excellent marker for foetal and resident macrophages in brain and many non-lymphoid organs. It is weakly expressed by blood monocytes and alveolar macrophages, and is absent in osteoclasts. F4/80 is also present in the liver (Kupffer cells), lamina propria (gut), splenic red pulp, lymph nodes (medulla), brain (microglia), bone marrow stroma, and Langerhans cells in the skin. RT-PCR data show that F4/80 undergoes extensive RNA splicing. As with other members of the EGF-TM7 family the majority of splicing events at the 5' end of the gene, producing several different potential protein isoforms. The putative protein isoforms contain differing numbers and/or arrangements of membrane-bound or soluble forms of N-terminal EGF domains.

The founding member of the EGF-TM7 family, CD97,is a B and T cell activation antigen expressed constitutively by human granulocytes, monocytes, at low levels by resting T and B cells and is markedly and rapidly upregulated upon T and B cell activation. In addition to its predominantly leukocyte-restricted nature, CD97 expression is also detected on non-leukocytes such as smooth muscle cells. CD97 occurs on the cell surface as three major isoforms resulting from alternative RNA splicing. Its binding partner CD55 is a member of the Regulators of Complement Activation (RCA) family. These proteins contain short consensus repeats (SCRs), a protein module commonly found in ~0.3% of all proteins, mostly but not exclusively in proteins of the complement system. CD55 is known to protect host cells from complement mediated damage by binding to C3b and C4b and preventing the formation of C3 convertases.

EMR2 shares extremely high homology with CD97,differing by only six amino acids within its EGF domains. As with CD97,it occurs as various alternative splice forms containing different numbers and arrangements of membrane-bound and soluble EGF domains. However, unlike CD97 its expression profile is restricted to neutrophils, DCs and culture-derived macrophages. The longest isoform of EMR2 and CD97 have recently been shown to bind certain forms of the glycosaminoglycan, chondroitin sulphate, which may be used as the subject macrophage targeting moiety. Chondroitin sulphate is a major component of extracellular matrix and is often found on cell surface proteoglycans. The binding of EMR2/CD97-bearing neutrophil and macrophage suggests a mechanism whereby these phagocytes migrate during inflammation or wound repair.

EMR3 consists of EGF repeats coupled to a G-protein coupled receptor moiety, and shares a high degree of homology to EMR2 within its transmembrane region. RNA data have shown EMR3 to be restricted to polymorphonuclear cells and culture derived macrophages.

The full-length mouse EMR4 cDNA encodes a predicted 689 amino acid protein containing two EGF-like modules, a mucin-like spacer domain, and a seven-transmembrane domain with a cytoplasmic tail. Similar to F4/80, mEMR4 is predominantly expressed on resident macrophages. The expression of mEMR4 is up-regulated following macrophage activation in biogel and thioglycollate-elicited peritoneal macrophages. Similarly, mEMR4 is over-expressed in TNF-a treated resident peritoneal macrophages while IL-4 and IL-10 dramatically reduce the expression. Using multivalent biotinylated mEMR4-mFc fusion proteins as a probe, a putative cell surface ligand was identified on a B lymphoma cell line, A20,in a cell-binding assay. Such ligand may be used as a macrophage-targeting moiety of the invention.

Sialoadhesin (Sn) is a macrophage adhesion molecule containing 17 extracellular Immunoglobulin-like domains. It is an I-type lectin which binds to sialic acid ligands expressed on haematopoietic cells. Thus sialic acid ligands or Sialoadhesin-specific antibodies may be used as the subject macrophage-targeting moieties.

Sialoadhesin may not be expressed on all macrophages. Expression is seen best on macrophages of the marginal zone in the spleen and the subcapsular sinus of lymph nodes. This section (Sn spleen) of a normal spleen stained with anti sialoadhesin MAb SER4 shows clearly the Sn staining only in macrophages of the marginal zone and no staining of macrophages in the white pulp areas (wp) or only weak staining of red pulp (rp) areas. It also identifies subsets of macrophages in bone marrow stroma; subcapsular sinus of lymph nodes and marginal metallophils. Thus such antibody may be used to restrict the delivery to specific subset of macrophages.

Macrosialin (murine equivalent of CD68) is a pan-macrophage late endosomal glycoprotein also expressed by some myeloid-derived dendritic cells. It is related to the lysosomal associated meosteoclastsmbrane protein (Lamp) family, but is more restricted to macrophages by virtue of an extracellular mucin-domain. It is heavily glycosylated (O- and N-linked structures), and glycoforms are markedly remodeled by phagocytic and inflammatory stimuli. Macrosialin binds oxidized lipoprotein (a subject macrophage-targeting moieties).

Scavenger Receptor A is expressed on many mature tissue macrophages and hepatic sinusoidal endothelium. Strong expression is found on alveolar macrophages and perivascular microglia.

Mannose receptor is expressed by macrophages and nonvascular endothelium. (Martinez-Pomares L, Reid, D M, Brown G D, Taylor P R, Stillion R J, Linehan S A, Zamze S, Gordon S & Wong S Y. Analysis of mannose receptor regulation by IL-4,IL-10,and proteolytic processing using novel monoclonal antibodies. J. Leukoc. Biol. 2003. 73: 604-613). Antibody is available through Serotec.

Type 3 Complement Receptor (5C6) is expressed by monocytes, neutrophils and NK cells. It is down-regulated on tissue macrophages except on microglia. It is present on granuloma and inflammatory macrophages. Ab 5C6 blocks myelomonocytic adhesion to serum-coated bacteriologic plastic in vitro and myelomonocytic cell recruitment in vivo, as well as iC3b rosetting.

Ag 7/4 is expressed by PMNs, monocytes and on some activated macrophages. It is extremely useful for the identification of recruited monocytes during inflammation (Taylor et al., Eur. J. Immunol. 33: 2090-2097, 2003; Henderson et al. Blood 102: 328-335).

Dectin-1,the b-glucan receptor, is expressed by most macrophages, monocytes, neutrophils, subsets of dendritic cell and a subset of T cells (Taylor et al. J. Immunol. 169: 3876-3882, 2002). Antibody to Dectin-1 is available through Serotec.

Several non-limiting examples of receptors on dendritic cells that can be targeted by ligands or antibodies include C-type lectin receptors such as mannose receptors, Dec-205 receptors, Fc receptors and Toll-like receptors.

4.RNAi Constructs and Modifications i) General Characteristics of Duplex Structure The subject RNAi constructs, in general, can be any constructs that induces RNA interference in vivo, such as in a mammalian cell. In certain embodiments, a subject RNAi construct may be single stranded, double stranded, DNA, RNA, a hybrid thereof, an RNAi agent, an siRNA agent, a short hairpin RNAi agent (shRNA), microRNA agent (miRNA), morpholino, or combination thereof, to either restore, diminish, or modulate gene function, as appropriate. The agents are delivered using the delivery system of the invention, either alone, in combination with other delivery system of the invention, such that the desired cell, cellular or biological space, or tissue targeting (e.g., macrophage or macrophage-like cell) is achieved.

Double-stranded oligonucleotides of the invention may be formed by two separate complementary nucleic acid strands. Duplex formation can occur either inside or outside the cell containing the target gene.

As used herein, the term "double-stranded" includes one or more nucleic acid molecules comprising a region of the molecule in which at least a portion of the nucleomonomers are complementary and hydrogen bond to form a duplex.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14,or 15 mismatches.

ii) Other Characteristics of siRNA

The nucleic acid molecules or constructs of the invention include dsRNA molecules comprising 16-30,e.g., 16, 17, 18, 19, 20, 21, 22, 23, 24, 25, 26, 27, 28, 29,or 30 nucleotides in each strand, wherein one of the strands is substantially complementary to, e.g., at least 80% (or more, e.g., 85%, 90%, 95%, or 100%) (for example, having 3, 2, 1,or 0 mismatched nucleotide(s)), to a target region, such as a target region that differs by at least one base pair between the wild type and mutant allele of a nucleic acid sequence. For example, the target region can comprise a gain-of-function mutation, and the other strand is identical or substantially identical to the first strand. The dsRNA molecules of the invention can be chemically synthesized, or can be transcribed in vitro from a DNA template, or in vivo from an engineered RNA precursor, e.g., shRNA. The dsRNA molecules can be designed using any method known in the art.

In one aspect, the invention provides a double-stranded RNA (dsRNA) construct of 19-49 nucleotides in length, for inhibiting expression of a target gene, the dsRNA comprising: (1) a sense strand having a 5'-end and a 3'-end, wherein one or more nucleotides at each of the 5'- and 3'-ends of the sense strand have 2'-modified ribose sugars, and, (2) an antisense strand having a 5'-end and a 3'-end, which hybridizes to the sense strand and to mRNA of the target gene, wherein (a) the dsRNA is resistant to cleavage by Dicer, (b) the antisense strand associates with RISC, and (c) the dsRNA inhibits expression of the target gene in a sequence-dependent manner.

It has been shown by Applicants that certain longer dsRNAs (e.g., those with a double-stranded region of more than 21 base pairs) are not cleaved by Dicer or other Dicer-like RNAse III when the sense strands are modified (e.g., at both ends of the sense strand by, for example, 2'-O-methyl groups), and that the antisense strands of such dsRNAs can be loaded into the RISC complex, with the 5'-ends of the antisense strands aligning with the 5'-end of a 21-mer (i.e., the Dicer cleavage product). While the art taught that RNAi activity was increased (compared to siRNA) if the compound formed a substrate for Dicer, some RNAi compounds that are not Dicer substrates have been shown to be extremely active. RISC complex loaded with such a longer antisense (guide) strand will cleave the target mRNA at a single position corresponding to the position between the 10th and 11th nucleotides from the 5'-end of the antisense (guide) sequence. One implication of this design is that the antisense strand of such a longer dsRNA becomes the single species of active RNAi reagent, thus facilitating the development of RNAi reagents or therapeutics with higher target specificity, and better-defined biological activity and/or pharmacological property. It is thus desirable to apply such dsRNAs as part of the present delivery system.

Furthermore, with the knowledge that longer dsRNA can be engineered to resist Dicer cleavage, and the knowledge that the Dicer-resistant antisense strand can be loaded onto the RISC complex at defined location to create a single species of active RNAi reagent, one can engineer additional features or modifications into the sense and/or antisense strands to improve the property of the RNAi reagent or therapeutics. In particular, the positioning of modifications in the guide strand relative to the 5' end can now be defined, and this positioning is critical to defining the specificity and activity of such modified RNAi compounds.

In certain embodiments, the antisense strand is unmodified. In other embodiments, the antisense strand includes a 2'-modified ribose sugar at the 2nd nucleotide from the 5'-end of the antisense strand. As used herein, "2'-modified ribose sugar" includes those ribose sugars that do not have a 2'-OH group. For example, the 2'-modified ribose sugar may be 2'-O-alkyl nucleotides, 2'-deoxy-2'-fluoro nucleotides, 2'-deoxy nucleotides, 2'-H (deoxyribonucleotides), or combination thereof.

In certain embodiments, the dsRNA of the invention with the above-referenced antisense modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified antisense modification, thus greatly improving the overall specificity of the RNAi reagent or therapeutics. As used herein, "off-target" gene silencing refers to unintended gene silencing due to, for example, spurious sequence homology between the antisense (guide) sequence and the unintended target mRNA sequence.

In another aspect, the invention provides a double-stranded RNA (dsRNA) construct of 19-49 nucleotides in length, for inhibiting expression of a target gene, the dsRNA comprising: (1) a sense strand having a 5'-end and a 3'-end, wherein one or more nucleotides at each of the 5'- and 3'-ends of the sense strand have 2'-modified ribose sugars, and, (2) an antisense strand having a 5'-end and a 3'-end, which hybridizes to the sense strand and to mRNA of the target gene, wherein the antisense strand comprises, at the 3'-end of the antisense strand, (i) at least four consecutive 2'-modified ribose sugars with non-hydrolyzable internucleotide linkages, (ii) 1, 2, 3, 4, 5, 6, 7, 8, 9, 10, 11,or 12 2'-modified ribose sugars, preferably 2'-O-methyl modified ribose sugars, or, (iii) a protective group, wherein (a) the dsRNA is resistant to cleavage by Dicer, (b) the antisense strand associates with RISC, and (c) the dsRNA inhibits expression of the target gene in a sequence-dependent manner.

According to this aspect of the invention, certain antisense modifications further increase nuclease stability, and/or lower interferon induction, without significantly decrease RNAi activity (or no decrease in RNAi activity at all). In another aspect, the invention provides a double-stranded RNA (dsRNA) construct of 19-49 nucleotides in length, for inhibiting expression of a target gene, the dsRNA comprising: (1) a sense strand having a 5'-end and a 3'-end, wherein one or more nucleotides at each of the 5'- and 3'-ends of the sense strand have 2'-modified ribose sugars, and the sense strand comprises a mismatch nucleotide at the 2nd nucleotide from the 3'-end of the sense strand, and, (2) an antisense strand having a 5'-end and a 3'-end, which hybridizes to the sense strand and to mRNA of the target gene, wherein (a) the dsRNA is resistant to cleavage by Dicer, (b) the antisense strand associates with RISC, and (c) the dsRNA inhibits expression of the target gene in a sequence-dependent manner.

According to this aspect of the invention, certain mismatches at the 3'-end of the sense strand allow more efficient loading of the antisense strand into the RISC complex, thus leading to more potent RNAi activity. Preferred such sense strand mismatches include: a mismatch at the second to the last nucleotide of the sense strand (which base pairs with the second nucleotide of the Dicer-resistant antisense strand in the RISC complex); and mismatches at the most 3'-end 9 nucleotides, except for the most 3'-end nucleotide, of the sense strand.

It is contemplated that different features of the invention, such as the different sense and/or antisense strand modifications, may be combined except when indicated otherwise, in order to create RNAi constructs with multiple advantages or features over the conventional siRNA constructs. For example, for all applicable aspects of the invention, the antisense strand may comprise a 2'-modified ribose sugar, such as 2'-O-methyl modified nucleotide, at the $2^{nd}$ nucleotide on the 5'-end of the antisense strand and, preferably no other modified nucleotides. The dsRNA having such modification may have enhanced target specificity or reduced off-target silencing compared to a similar construct without the 2'-O-methyl modification at the position.

For all applicable aspects of the invention, the antisense strand may comprise at least four consecutive 2'-modified ribose sugars, such as 2'-O-methyl modified, 3'-end nucleotides with non-hydrolyzable internucleotide linkages, such as phosphothioate linkages. For all applicable aspects of the invention, the dsRNA may be cleaved by RISC at a single site between the $10^{th}$ and $11^{th}$ nucleotides of the 3'-end of the sense strand. For all applicable aspects of the invention, the 5'-end 12 nucleotides and the 3'-end 10 nucleotides of a 25-mer may be 2'-modified ribose sugars. The number of the modified bases may be adjusted depending on the overall length of the construct. For example, for a 27-mer, the 5'-end 12-14 nucleotides and the 3'-end 10-12 nucleotides may be 2'-modified nucleotides, etc. For all applicable aspects of the invention, the dsRNA may comprise a mismatch nucleotide at the $2^{nd}$ nucleotide from the 3'-end of the sense strand.

Certain combinations of specific antisense and sense strand modifications may even result in unexpected advantages, as partly manifested by enhanced ability to inhibit target gene expression, enhanced serum stability, and/or increased target specificity, etc. Thus, in another aspect, the invention provides double-stranded RNA (dsRNA) construct of 19-49 nucleotides in length, for inhibiting expression of a target gene, the dsRNA comprising: (1) a sense strand having a 5'-end and a 3'-end, wherein four consecutive 2'-O-methyl nucleotides are present at each of the 5'- and 3'-ends of the sense strand, and, (2) an antisense strand having a 5'-end and a 3'-end, which hybridizes to the sense strand and to mRNA of the target gene, wherein the antisense strand: (a) comprises four consecutive 2'-O-methyl modified 3'-end nucleotides with phosphothioate linkages; or, (b) comprises a 2'-O-methyl modified nucleotide at the 2nd nucleotide on the 5'-end and no other modified nucleotides, wherein (a) the dsRNA is resistant to cleavage by Dicer, (b) the antisense strand associates with RISC, and (c) the dsRNA inhibits expression of the target gene in a sequence-dependent manner.

In another aspect, the invention provides a double-stranded RNA (dsRNA) construct of 19-49 nucleotides in length, for inhibiting expression of a target gene, the dsRNA comprising: (1) a sense strand having a 5'-end and a 3'-end, wherein the sense strand comprises 12 and 10 consecutive 2'-O-methyl nucleotides at the 5'-end and the 3'-end, respectively, and, (2) an antisense strand having a 5'-end and a 3'-end, which hybridizes to the sense strand and to mRNA of the target gene, wherein the antisense strand: (a) is unmodified; (b) comprises four consecutive 2'-O-methyl modified 3'-end nucleotides with phosphothioate linkages; or, (c) comprises a 2'-O-methyl modified nucleotide at the 2nd nucleotide on the 5'-end and no other modified nucleotides, wherein (a) the dsRNA is resistant to cleavage by Dicer, (b) the antisense strand associates with RISC, and (c) the dsRNA inhibits expression of the target gene in a sequence-dependent manner.

In certain embodiments, the antisense strand of the subject dsRNA directs the uniform cleavage of the target gene transcript at a single site between the $10^{th}$ and $11^{th}$ nucleotides from the 5'-end of the antisense strand. In certain embodiments, the sense strand of the dsRNA is cleavable by RISC at a single site between the 10th and the 11th nucleotides from the 3'-end of the sense strand.

According to this embodiment of the invention, certain sense strand sequences may be cleaved by the RISC complex loaded with the Dicer-resistant guide sequence, at the position where an equivalent mRNA is cleaved. While not wishing to be bound by any particular theory, this is partly because the sense strand share the same or similar sequence as the target mRNA. Therefore, the subject dsRNA constructs include those with a sense strand that can be cleaved between the 10th and 11th 3'-end nucleotides.

The constructs of the invention may have different lengths. In certain embodiments, the preferred lengths of the construct are 19-49 nucleotides in length. In certain embodiments, the length of the construct is greater than or equal to 22 nucleotides in length. In certain embodiments, the length of the construct is greater than or equal to 25 nucleotides in length. In certain embodiments, the length of the construct is 26, 27, 28, 29, 30,or 31-49 nucleotides in length. Other lengths are also possible, so long as the lower length limit is the minimal length for a Dicer substrate, and the upper limit is a length that generally will not trigger PKR response in a target cell. In certain embodiments, modifications may alter that upper limit such that longer lengths (such as 50, 60, 70, 80, 90, 100 bp) are tolerable.

In certain embodiments, the dsRNA construct is blunt-ended. In other embodiments, 5'- and/or 3'-end overhangs of 1-4 nucleotides may be present on one or both strands. For a 25-mer construct, each end of the sense strand may comprise, independently, 4-16 2'-modified nucleotides and/or non-hydrolyzable linkages (e.g., phosphothioate linkages). The number of the modified bases may be adjusted depending on the overall length of the construct. For example, for a 27-mer, each end of the sense strand may comprise, independently, 4-18 2'-modified nucleotides and/or phosphothioate linkages, etc. In certain embodiments, the 5'-end 12 nucleotides and the 3'-end 10 nucleotides of the sense strand are 2'-modified ribose sugars.

In certain embodiments, each end of the sense strand comprises a continuous stretch of 2'-modified ribose sugars, although each end may have the same number or different numbers of 2'-modified ribose sugars. In certain embodiments, each end of the sense strand comprises a continuous stretch of four 2'-modified ribose sugars. In certain embodiments, the antisense strand comprises discontinuous 2'-modified ribose sugars, wherein the 10th and 11th antisense nucleotides are not modified. For example, the antisense strand may comprises 2'-modified ribose sugars for each 2, 3, 4, 5, 6, 7, 8,or 9 nucleotides. The most 5'-end 2'-modified ribose sugar on the antisense strand may be the 2nd nucleotide, or the first nucleotide.

In certain embodiments, the 2'-modified nucleotides are 2'-O-alkyl nucleotides, 2'-deoxy-2'-fluoro nucleotides, 2'-deoxy nucleotides, 2'-H (deoxyribonucleotide), or combination thereof. In certain embodiments, the 2'-modified nucleotides are pyrimidine nucleotides (e.g., C/U). For example, the 2'-O-alkyl nucleotides may be 2'-O-methyl nucleotides, or 2'-O-allyl nucleotides. In certain embodiments, the antisense strand comprises a 2'-O-methyl modified nucleotide at the $2^{nd}$ nucleotide on the 5'-end of the antisense strand and no other modified nucleotides.

In certain embodiments, the modified dsRNA may have improved stability in serum and/or cerebral spinal fluid compared to an unmodified dsRNA having the same sequence. In certain embodiments, the dsRNA has enhanced target specificity or reduced off-target silencing compared to a similar construct without the 2'-modification at the position(s). In certain embodiments, the antisense strand comprises at least four consecutive 2'-O-methyl modified 3'-end nucleotides with phosphothioate linkages. In certain embodiments, the sense strand of the dsRNA comprises a mismatch nucleotide at the $2^{nd}$ nucleotide from the 3'-end of the sense strand. In certain embodiments, the last $2^{nd}$-$8^{th}$ nucleotides at the 3'-end of the sense strand mis-match their corresponding antisense strand nucleotides.

In certain embodiments, the dsRNA does not induce interferon response in primary cells, such as mammalian primary cells, including primary cells from human, mouse and other rodents, and other non-human mammals. In certain embodiments, the dsRNA may also be used to inhibit expression of a target gene in an invertebrate organism. In certain embodiments, the 10th and 11th antisense nucleotides from the 5'-end are not modified.

To further increase the stability of the subject constructs in vivo, either end of the sense strand and/or the 3'-end of the antisense strand may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

In certain embodiments, alternating nucleotides on the ends of the sense and antisense strands are modified by 2'-O-alkyl modification, and wherein each of the 2'-O-modified nucleotides faces an unmodified nucleotide on the opposite strand. In a preferred embodiment, the first 2'-O-modified antisense nucleotide (with this pattern of modification) is the most 5'-end antisense nucleotide. In certain embodiments, alternating nucleotides on the ends of the sense and/or antisense strands comprise 2'-modified ribose sugars, and wherein each of the 2'-modified ribose sugars faces an unmodified nucleotide on the opposite strand. In certain embodiment, the first 2'-modified antisense nucleotide is the most 5'-end antisense nucleotide or the 2nd nucleotide from the 5'-end of the antisense strand. In certain embodiments, RNAi constructs having the same or similar structures of any of the Alternate RNAi Compounds described herein, but differing by not being resistant to Dicer cleavage, are also desirable, so long as they show high activity against their respective intended target (e.g., mRNA).

In certain embodiments, the subject double-stranded RNA may be chemically cross-linked at one or more points, or linked by a nucleotide loop structure at one or both ends (e.g., a single-stranded hairpin structure or a circular structure). In one embodiment, the chemical cross-link or the loop of the hairpin structure is at the 3'-end of the antisense strand (e.g., linking the 3'-end of the antisense strand to the 5'-end of the sense strand). In another embodiment, the chemical cross-link or the loop of the hairpin structure is at the 5'-end of the antisense strand (e.g., linking the 3'-end of the sense strand to the 5'-end of the antisense strand. In these embodiments, other structural features of the cross-linked or looped constructs, such as 5'-end and 3'-end modifications on the sense strand and/or the other modifications on the antisense strand, are essentially the same as those for the dsRNA described herein.

Double-stranded and/or duplex oligonucleotide constructs of the invention are capable of inhibiting the synthesis of any target protein encoded by target gene(s). The invention includes methods to inhibit expression of a target gene either in a cell in vitro, or in vivo. The target gene can be endogenous or exogenous (e.g., introduced into a cell by a virus or using recombinant DNA technology) to a cell. Such methods may include introduction of RNA into a cell in an amount sufficient to inhibit expression of the target gene, where the RNA is a double-stranded duplex. By way of example, such an RNA molecule may have a first strand having a ribonucleotide sequence that corresponds to a nucleotide sequence of the target gene, and a second strand having a ribonucleotide sequence that is complementary to the nucleotide sequence of the target gene, in which the first and the second strands are separate complementary strands, and they hybridize to each other to form the double-stranded molecule, such that the duplex composition inhibits expression of the target gene.

The invention also relates to vectors expressing at least one strand of the subject dsRNA constructs, and cells comprising such vectors or the subject dsRNA constructs. The cell may be a mammalian cell in culture, such as a human cell. The invention further relates to compositions comprising the subject dsRNA constructs, and a pharmaceutically acceptable carrier or diluent. Another aspect of the invention provides a method for inhibiting the expression of a target gene in a mammalian cell, comprising contacting the mammalian cell with the any of the subject dsRNA constructs.

iii) Modifications to RNAi Constructs

The nucleotides of the invention may be modified at various locations, including the sugar moiety, the phosphodiester linkage, and/or the base.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a nonnaturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$,), or CN group, wherein R is lower alkyl, alkenyl, or alkynyl.

Modified ribonucleotides may also have the phosphoester group connecting to adjacent ribonucleotides replaced by a modified group, e.g., of phosphothioate group. More generally, the various nucleotide modifications may be combined.

In one embodiment, sense oligomers may have 2'-modifications on the ends (e.g., 2 on each end, 3 on each end, and 4 on each end, etc.; as well as 1 on one end, 2 on one end, 3 on one end, and 4 on one end, etc.; and even unbalanced combinations such as 12 on one end and 10 on the other end, etc.). Likewise, the antisense strand may have 2'-modifications on the ends (1 on each end, 2 on each end, 3 on each end, and 4 on each end, and so on; as well as 1 on one end, 2 on one end, 3 on one end, and 4 on one end, and so on; and even unbalanced combinations such as 1 on one end and 2 on the other end, and so on). In preferred aspects, the 2'-modifications are 2'-O-methyl modifications in the sense RNA strand and/or the antisense strand.

According to the instant invention, the sense strand can tolerate many 2'-modifications (such as 2'-O-methyl modifications), so long as the central linkages are unmodified. As used herein, "central" is not limited to mean the geometric mid-point of the sense strand. Rather, it can include any location between the 5'-end portion and the 3'-end portion of the sense strand. The 5'-end portion and the 3'-end portion of the sense strand need not be symmetrical.

Thus, in certain embodiments, the sense strand is not completely modified (i.e., at least one or more sense strand nucleotide(s) are unmodified). In certain embodiments, the unmodified sense strand nucleotides are in the central portion of the sense strand, or between the stretch of modified sense strand nucleotides on the 5'-end and the stretch of modified sense strand nucleotides on the 3'-end.

Also according to the instant invention, the sense strand tolerance for 2'-modification is not necessarily symmetrical. Rather, asymmetrical configurations may be desirable when using, for example, a sense strand of 25 or 26 nucleotides. 2'-mofications add nuclease stability, and reduce interferon induction, and are easier to synthesize. Thus it may be desirable to include more such 2'-modified ribose sugars (especially 2'-O-methyl modified) on the sense strand, so long as the teachings of the instant invention is followed to preserve RNAi activity.

In some embodiments of the present invention, the subject highly modified sense strands may be combined with either unmodified or lightly modified antisense strands to allow maximum guide strand activity.

To further maximize endo- and exo-nuclease resistance, in addition to the use of 2'-modified nucleomonomers in the ends, inter-nucleomonomer linkages other than phosphodiesters may be used. For example, such end blocks may be used alone or in conjunction with phosphothioate linkages between the 2'-O-methly linkages. Preferred 2'-modified nucleomonomers are 2'-modified end nucleotides.

Although the antisense strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

One particular example of a composition of the invention has end-blocks on both ends of a sense oligonucleotide and only the 3'-end of an antisense oligonucleotide. Without wishing to be bound by theory, a 2'-O-modified sense strand may work less well than its unmodified version, possibly because it is not efficiently unwound. Thus, in certain embodiments, mismatches may be introduced into specific positions of the sense strand (modified 2'-O-methyl sense strand, or even unmodified sense strand) to facilitate easier loading into the RISC complex.

In some embodiments, the length of the sense strand can be 30, 29, 28, 27, 26, 25, 24, 23, 22, 21, 20, 19,or 18 nucleotides. Similarly, the length of the antisense strand can be 30, 29, 28, 27, 26, 25, 24, 23, 22, 21, 20, 19,or 18 nucleotides. Further, when a double-stranded nucleic acid molecule is formed from such sense and antisense molecules, the resulting duplex may have blunt ends or overhangs of 0, 1, 2, 3, 4, 5, 6, 7, 8, 9, 10, 11, 12, 13,or 14 nucleotides on one end or independently on each end. Further, double stranded nucleic acid molecules of the invention may be composed of a sense strand and an antisense strand wherein these strands are of lengths described above, and are of the same or different lengths, but share only 10, 11, 12, 13, 14, 15, 16, 17, 18, 19,or 20 nucleotides of sequence complementarity. By way of illustration, in a situation where the sense strand is 20 nucleotides in length and the antisense is 25 nucleotides in length and the two strands share only 15 nucleotides of sequence complementarity, a double stranded nucleic acid molecules may be formed with a 10 nucleotide overhang on one end and a 5 nucleotide overhang on the other end.

The use of 2'-O-methyl RNA may also be beneficially in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—OCH$_2$CH=CH$_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O— (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R'' are each independently hydrogen, a $C_1$-$C_5$ alkyl, $C_2$-$C_5$ alkenyl, $C_2$-$C_5$ alkynyl, or aryl group, or R' and R'' taken together are a benzylidene group or a —$(CH_2)_2$O$(CH_2)_2$-group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The term "base" includes the known purine and pyrimidine heterocyclic bases, deazapurines, and analogs (including heterocyclic substituted analogs, e.g., aminoethoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl)cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligunucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", 2"Ed., Wiley-Interscience, New York, 1999).

The term "nucleotide" includes nucleosides which further comprise a phosphate group or a phosphate analog.

As used herein, the term "linkage" includes a naturally occurring, unmodified phosphodiester moiety (—O—($PO^{2-}$)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991.Nucleic Acids Res. 19:5843; Caruthers et al. 1991.Nucleosides Nucleotides. 10:47). In certain embodiments, non-hydrolizable linkages are preferred, such as phosphorothiate linkages.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849, 902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$-$CH_2$-$CH_3$), glycol (—O—$CH_2$-$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3' linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In one embodiment, the sense strand of an oligonucleotide comprises a 5' group that allows for RNAi activity but which renders the sense strand inactive in terms of gene targeting. Preferably, such a 5' modifying group is a phosphate group or a group larger than a phosphate group. Oligonucleotides of this type often exhibit increased specificity for a target gene in a cell that corresponds to the nucleotide sequence of the antisense strand. This is because the sense strand in such an oligonucleotide is often rendered incapable of mediating cleavage of any nucleotide sequence it might bind to non-specifically and thus will not inactivate any other genes in the cell. Thus, observed decrease in the expression of a gene within a cell transfected with such an oligonucleotide will often be attributed to the direct or indirect effect of the antisense strand. The term "specificity for a target gene," as used herein means the extent to which an effect of an oligonucleotide on a cell can be attributed directly or indirectly to the inhibition of expression of a target gene by an antisense nucleotide sequence present in the oligonucleotide.

Thus, according to another embodiment, the invention provides a method of increasing the specificity of an oligonucleotide for a target gene in a cell, wherein the oligonucleotide comprises a sense strand and an antisense strand, wherein both the sense strand and the antisense strand are capable of binding to corresponding nucleotide sequences if present in the cell, the method comprising the step of modifying the 5' terminal hydroxy moiety of the sense strand with a phosphate group or a group larger than a phosphate group prior to contacting the oligonucleotide with the cell so as to render the sense strand incapable of mediating cleavage of any nucleotide sequence it might bind to non-specifically and thus will not inactivate any other genes in the cell.

Another way to increase target gene specificity, or to reduce off-target silencing effect, is to introduce a 2'-modification (such as the 2'-O methyl modification) at a position corresponding to the second 5'-end nucleotide of the Dicer-cleaved 21-mer. Applicants' discovery allows the positioning of this 2'-modification in the Dicer-resistant dsRNA, thus enabling one to design better siRNA constructs with less or no off-target silencing.

In one embodiment, a double-stranded oligonucleotide of the invention can comprise (i.e., be a duplex of) one nucleic acid molecule which is DNA and one nucleic acid molecule which is RNA. Antisense sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide. In one embodiment, at least a portion of the contiguous polynucleotides are linked by a substitute linkage, e.g., a phosphorothioate linkage.

In certain embodiments, most or all of the sense strand nucleotides (2'-modified or not) are linked by phopshorothioate linkages. Such constructs tend to have improved pharmaco-kinetics due to their higher affinity for serum proteins. The phosphothiaote linkages in the sense strand generally do not interfere with guide strand activity, once the latter is loaded into RISC.

Antisense sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate intersubunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

In further embodiments of the invention, the RNAi constructs may be modified to include cationic polymers. In general, a cationic polymer is a polymer that is positively charged at approximately physiological pH, e.g., a pH ranging from approximately 7.0 to 7.6, preferably approximately 7.2 to 7.6, more preferably approximately 7.4. Such cationic polymers include, but are not limited to, polylysine (PLL), polyarginine (PLA), polyhistidine, polyethyleneimine (PEI), including linear PEI and low molecular weight PEI as described, for example, in polyvinylpyrrolidone (PVP) and chitosan. It will be appreciated that certain of these polymers comprise primary amine groups, imine groups, guanidine groups, and/or imidazole groups. Preferred cationic polymers have relatively low toxicity and high DNA transfection efficiency.

Suitable cationic polymers also include copolymers comprising subunits of any of the foregoing polymers, e.g., lysine-histidine copolymers, etc. The percentage of the various subunits need not be equal in the copolymers but may be selected, e.g., to optimize such properties as ability to form complexes with nucleic acids while minimizing cytotoxicity. Furthermore, the subunits need not alternate in a regular fashion. Preferred cationic polymers also include polymers such as the foregoing, further incorporating any of various modifications. Appropriate modifications include, but are not limited to, modification with acetyl, succinyl, acyl, or imidazole groups.

The siRNAs of the invention include both siRNA and crosslinked siRNA derivatives as described in U.S. Provisional Patent Application No. 60/413,529, which is incorporated herein by reference in its entirety. Crosslinking can be employed to alter the pharmacokinetics of the composition, for example, to increase half-life in the body. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivates has at its 3' terminus a biotin molecule (e.g., a photocleavable biotin), a peptide (e.g., a Tat peptide), a nonoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCERTM siRNA labeling kit (Ambion). Additionally, the siRNA can be radiolabeled, e.g., using 3H, 32P, or other appropriate isotope.

Nucleic acid molecules recited herein comprise nucleotide sequences with or without 3' overhangs, e.g., with or without 3'-deoxythymidines. Other embodiments are also envisioned in which the 3' overhangs comprise other nucleotides, e.g., UU or the like.

iv) Peptide Conjugates of siRNA

The siRNAs of the present invention, as well as an engineered RNA precursor or engineered nucleic acid molecules that encode the precursors, can be conjugated to delivery peptides or other compounds to enhance the efficiency of transport of the siRNA into living cells in combination with the present delivery system. These delivery peptides can include peptides known in the art to have cell-penetrating properties. For instance, the delivery peptide can be, but is not limited to: TAT derived short peptide from human immunodeficiency virus (HIV-1), such as TAT 47-57 and Cys (CYGRKKRRQRRR) (SEQ ID NO:1), and TAT 49-60 and (Arg)$_9$ (Tat) (RKKRRQRRRPPQC) (SEQ ID NOs:2 & 3), and substantially similar functional variants thereof, e.g., a functional variant that is at least 65% identical thereto. Of course, the percent identity can be higher, e.g., 65%, 67%, 69%, 70%, 73%, 75%, 77%, 83%, 85%, 87%, 90%, 93%, 95%, 97%; 100% identity (for example, peptides with substitutions at 1, 2, 3, 4 or more residues) (e.g., CYQRKKRRQRRR) (SEQ ID NO:4). In general, the substitutions are conservative substitutions. The methods of making such peptides are routine in the art.

The delivery peptide can also be, but is not limited to: the third a-helix of Drosophila Antennapedia homeodomain (Ant) (RQIKIWFQNRRMKWKKGGC) (SEQ ID NO:5) and substantially similar functional variants thereof; VP22 protein from herpes simplex virus (DAATATRGRSAAS-RPTERPRAPARSASRPRRPVE) (SEQ ID NO:6) and substantially similar functional variants thereof; Nuclear localization sequence (NLS) of simian virus 40 (SV-40) large T antigen and substantially similar functional variants thereof; designed peptides (synthetic and/or chimeric cell-penetrating peptides) and variants thereof, including the Pep-1 peptide, a 21-residue peptide carrier (KETWWETWWTEWSQP-KKKRKV) (SEQ ID NO:7) consisting of three domains: (1) a hydrophobic tryptophan-rich motif, for efficient targeting to the cell membrane; (2) NLS of SV40 large T antigen, to improve intracellular delivery and solubility of the peptide vector; and (3) a spacer domain (SQP), containing a proline residue, to improve the flexibility and the integrity of the two hydrophobic and hydrophilic domains mentioned above, and substantially similar functional variants thereof; the MPG/MPS delivery system a 27-residue synthetic peptide containing a hydrophobic domain derived from the fusion sequence of HIV gp41 and a hydrophilic domain derived from the nuclear localization sequence of SV40 T-antigen (GALFLG-WLGAAGST-MGAWSQPKKKRKV) (SEQ ID NO:8) and substantially similar functional variants thereof; membrane translocating sequences (MTSs) derived from the hydrophobic regions of the signal sequences from Kaposi's sarcoma fibroblast growth factor 1 (K-FGF) 18 and human b3 integrin 19,the fusion sequence of HIV-1 gp41; the signal sequence of the variable immunoglobulin light chain Ig(v) from Caftan crocodylus2l conjugated to NLS peptides originating from nuclear transcription factor kB (NF-kB)$_{22}$, Simian virus 40 (SV40) T-antigen23 or K-FGF; cell-penetrating peptide, containing 16 residues from the K-FGF MTS coupled to a F-kB NLS (ten residues) or coupled to the SV40 T-antigen NLS (12 residues), (AAVALLPAVLLALLAP (SEQ ID NO:9) and functional variants thereof; the MTS from Ig(v) light chain coupled via a peptidase sensitive linker to residues 127-132 of SV40 T-antigen and variants thereof; cell-penetrating peptides including but not limited to penetratin, PEN (43-58 of the homeodomain of D. melanogaster antennapedia transcription factor, ANTP), RQIKIWFQNRRMKWKK (SEQ ID NO:10) and substantially similar functional variants thereof; signal-sequence-based peptides (I) (GALFLGWL-GAAGSTMGAWSQPKKKRKV) (SEQ ID NO:11) and functional variants thereof; signal-sequence-based peptides (II) (AAVALLPAVLLALLAP) (SEQ ID NO:12) and functional variants thereof; transportan (GWTLNSAGYLLKIN-LKALAALAKKIL) (SEQ ID NO:13) and variants thereof; galparan, a fusion between the neuropeptide galanin-1-13 and the wasp venom peptide mastoparans and substantially similar functional variants thereof; amphiphilic model peptide (KLALKLALKALKAALKLA) (SEQ ID NO:14); 18-mer amphipathic model peptide27; branched-chain arginine peptides and substantially similar functional variants thereof; 9-polylysine protein transduction domain and substantially similar functional variants thereof; b-peptide and functional variants thereof; shell cross-linked (SCK) nanoparticles combined with the oligomeric peptide sequence of the TAT protein transduction domain and substantially similar functional variants thereof. See US 20040204377 Al, incorporated herein by reference.

The peptides can also have modified backbones, e.g., oligocarbamate or oligourea backbones; see, e.g., Wang et al., J. Am. Chem. Soc., Volume 119,pp. 6444-6445,(1997); Tamilarasu et al., J. Am. Chem. Soc., Volume 121,pp. 1597-1598, (1999), Tamilarasu et al., Bioorg. Of Med. Chem. Lett., Volume 11,pp. 505-507,(2001).

5.Oligonucleotide Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. 1 *Am. Chem. Soc.* 106:6077; Stec et al. 1985.1 *Org. Chem.* 50:3908; Stec et al. J. Chromatog. 1985. 326:263; LaPlanche et al. 1986. *Nucl. Acid. Res.* 1986. 14:9081; Fasman G. D., 1989.Practical Handbook of Biochemistry and Molecular Biology. 1989.CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J. Med. Chem.* 36:831; WO 92/03568; U.S. Pat. Nos. 5,276,019; and 5,264,423.All incorporated herein by reference.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990,Chemical Reviews 90:543-584) provide references and outline procedures for making oligonucleotides with modified bases and modified phosphodiester linkages. Other exemplary methods for making oligonucleotides are taught in Sonveaux. 1994."Protecting Groups in Oligonucleotide Synthesis"; Agrawal. *Methods in Molecular Biology* 26:1.Exemplary synthesis methods are also taught in "Oligonucleotide Synthesis - A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982,1 *J. Am. Chem. Soc.* 104:976; Viari, et al., 1987, *Biomed. Environ.*

*Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. 1 Chrom. 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

The peptide conjugation discussed herein can be accomplished by methods known in the art, e.g., using the methods of Lambert et al. (2001), Drug Deliv. Rev., 47(1), 99-112 (describes nucleic acids loaded to polyalkylcyanoacrylate (PACA) nanoparticles); Fattal et al. (1998), J. Control Release, 53(1-3), 137-43 (describes nucleic acids bound to nanoparticles); Schwab et al. (1994), Ann. Oncol., 5 Suppl. 4, 55-8 (describes nucleic acids linked to intercalating agents, hydrophobic groups, polycations or PACA nanoparticles); and Godard et al. (1995), Eur. J. Biochem., 232(2), 404-10 (describes nucleic acids linked to nanoparticles). Peptide conjugates recited herein comprise peptide portions as set forth in the sequence listing with or without terminal cysteine residues.

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

6. Routes of Administration

Routes of administration for the subject delivery system include but are not limited to oral, buccal, sublingual, pulmonary, transdermal, transmucosal, as well as subcutaneous, intraperitoneal, intravenous, and intramuscular injection. Preferred routes of administration are oral and intramuscular injection.

The delivery system of the present invention is administered to a patient in a therapeutically effective amount. The delivery system can be administered alone or as part of a pharmaceutically acceptable composition. In addition, a compound or composition (e.g., the RNAi constructs with the payload trapping molecule) can be administered all at once, as for example, by a bolus injection, multiple times, such as by a series of tablets, or delivered substantially uniformly over a period of time, as for example, using a controlled release formulation. It is also noted that the dose of the compound can be varied over time. The subject delivery system can be administered using an immediate release formulation, a controlled release formulation, or combinations thereof The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the individual (e.g., human) treated, and further depending upon the route by which the composition is to be administered. By way of example, the composition can comprise between 0.1% and 100% (w/w) active ingredient. A unit dose of a pharmaceutical composition of the invention will generally comprise from about 100 milligrams to about 2 grams of the active ingredient, and preferably comprises from about 200 milligrams to about 1.0 gram of the active ingredient.

In addition, a subject delivery system of the invention can be administered alone, in combination with a particulate delivery system with a different payload, or with other pharmaceutically active compounds. The other pharmaceutically active compounds can be selected to treat the same condition as the particulate delivery system or a different condition.

If the patient is to receive or is receiving multiple pharmaceutically active compounds, the compounds can be administered simultaneously or sequentially in any order. For example, in the case of tablets, the active compounds may be found in one tablet or in separate tablets, which can be administered at once or sequentially in any order. In addition, it should be recognized that the compositions can be different forms. For example, one or more compounds may be delivered via a tablet, while another is administered via injection or orally as a syrup.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder- dispensing device, a syringe, a needle, a tampon, or a dosage- measuring container. The kit can further comprise an instructional material as described herein.

For example, a kit may comprise two separate pharmaceutical compositions comprising respectively a first composition comprising a particulate delivery system and a pharmaceutically acceptable carrier; and composition comprising second pharmaceutically active compound and a pharmaceutically acceptable carrier. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via the opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day. Also, a daily dose of a particulate delivery system composition can consist of one tablet or capsule, while a daily dose of the second compound can consist of several tablets or capsules and vice versa. The memory aid should reflect this and assist in correct administration.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

A subject delivery system composition, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. In preferred embodiments, the subject delivery system composition can be administered orally or parenterally, such as intramuscular injection.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di- glycerides. Other parentally-administrable formulations which are useful include those which comprise the active ingredient in microcrystalline form, in a liposomal preparation, or as a component of a biodegradable polymer system. Compositions for sustained release or implantation can comprise pharmaceutically acceptable polymeric or hydrophobic materials such as an emulsion, an ion exchange resin, a sparingly soluble polymer, or a sparingly soluble salt.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Solid dosage forms for oral administration include capsules, tablets, powders, and granules. In such solid dosage forms, the subject delivery system is optionally admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the particulate delivery system can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, polyvinylpyrrolidone, pre-gelatinized maize starch, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the particulate delivery system, e.g. in the region of the Peyer's patches in the small intestine. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the particulate delivery system in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the particulate delivery system can be made using a physiologically degradable composition, such as gelatin. Such hard capsules comprise the particulate delivery system, and can further comprise additional ingredients including, for example, an inert solid diluent such as calcium carbonate, calcium phosphate, or kaolin. Soft gelatin capsules comprising the particulate delivery system can be made using a physiologically degradable composition, such as gelatin. Such soft capsules comprise the particulate delivery system, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984,J. Med. Chem. 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the subject delivery system to a specific location within the gastrointestinal tract. Such systems permit delivery at a predetermined time and can be used to deliver the particulate delivery system, optionally together with other additives that my alter the local microenvironment to promote stability and uptake, directly without relying on external conditions other than the presence of water to provide in vivo release.

In further embodiments, the invention provides a delayed-release (DR) composition in an orally deliverable form, comprising an enteric coating, wherein the enteric coating reduces or substantially eliminates the release and/or absorption of the RNAi compound in the upper gastrointestinal (GI) tract. In certain embodiments, the RNAi compound is first released and/or absorbed in intestine. In certain embodiments, the enteric coating delays the release of the RNAi construct by at least about 1.5-2 hours, or 2-3 hours after ingestion.

Enteric coating may help eliminate the release of the RNAi compound in the stomach, such that the active agent is prevented from being prematurely released in the acidic environment of the stomach. Once inside the intestine, where the local pH environment based on the fed or fasted states varies between 4.5 and 7.4,the RNAi compound is released either as an immediate release (IR) dosage form or as an extended release (XR) dosage form, or a mixture thereof. Since such dosage forms are also delayed-release dosage forms, they are referred to as delayed immediate release (DIR or DR) or delayed extended release (DXR) dosage forms, respectively.

In certain embodiments, the dosage form may include bioadhesive layers that adhere to the lower GI tract, such as intestinal walls, to prolong the release of the active agent in the lower GI tract. The bioadhesive layer may be inside or outside the enteric coating. In the former case, the presence of the bioadhesive layer (e.g., as a partial coating that is continuous or discontinuous) preferably does not substantially impede the release of the active agent. In the latter case, the presence of the bioadhesive layer (e.g., as a partial coating that is continuous or discontinuous) does not substantially impede the degradation of the enteric layer in the neutral pH environment of the intestine.

In certain embodiments, the bioadhesive layer comprises polymeric materials selected from polyamides, polyalkylene glycols, polyalkylene oxides, polyvinyl alcohols, polyvinylpyrrolidone, polyglycolides, polyurethanes, polymers of acrylic and methacrylic esters, polylactides, poly(butyric acid), polyanhydrides, polyorthoesters, poly(fumaric acid), poly(maleic acid), polycarbonates, polyalkylenes, polyalkylene terephthalates, polyvinyl alcohols, polyvinyl ethers, polyvinyl esters, polyvinyl halides, polysiloxanes, polystyrene, poly(lactide-co-glycolide), chitosan, chitin, hyaluronic acid, hyaluronan, Carbopols, Corplex polymers, Polycarbophils-Cysteine (Thiomers), Chitosan-Thioglycolic acid copolymers, poly(methacrylic acid-grafted-ethylene glycol), poly (methyl vinyl ether-co-malic anhydride), cholestyramine (Duolite AP-143), sucralfate, gliadin, blends and copolymers thereof.

The compositions of the present invention may be in the form of, among others, a granule, tablet (including matrix or osmotic), pellet, powder, sachet, capsule, gel, dispersion, solution or suspension.

8. Dosage Forms i) Delayed release composition

The delayed-release component has a coat applied to the surface of the active pellet that delays the release of the drug from the pellet after administration for a certain period of time. This delayed release can be accomplished by applying a coating of enteric materials.

"Enteric materials" are polymers that are substantially insoluble in the acidic environment of the stomach, but are predominantly soluble in intestinal fluids at various specific pH's, such as pH 4.5 or higher. The enteric materials are non-toxic, pharmaceutically acceptable polymers, and include, for example, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, carboxymethyl ethylcellulose, Spheromer III, Spheromer IV, co-polymerized methacrylic acid/methacrylic acid methyl esters such as, for instance, materials known under the trade name EUDRAGIT® L12.5, L100,or EUDRAGIT® S12.5,S100, and several commercially available enteric dispersion systems (e.g., EUDRAGIT® L30D55,EUDRAGIT® FS30D, EUDRAGIT® L100-55, EUDRAGIT® S100 (Rohm Pharma), KOLLICOAT® MAE3OD and 30DP (BASF), ESTACRYL® 30D (Eastman Chemical), AQUATERIC® and AQUACOAT® CPD30 (FMC)), Acryl-EZE™ White, etc.

The foregoing is merely a list of possible enteric coating materials, but one of skill in the art would appreciate that there are other such materials that would meet the objectives of the present invention of providing for a delayed release profile, including tailoring release based on the ambient pH environment, temporal considerations and/or other factors.

These coating materials can be employed in coating the surfaces in a range of from about 1.0% (w/w) to about 50% (w/w) of the pellet composition. Preferably, these coating materials are in the range of from about 10-20% (w/w). The pellets may be coated in a fluidized bed apparatus or pan coating, for example, in a conventional manner.

With the enteric-coated pellets, there is no substantial release of the active agent in the acidic stomach environment of below about pH 4.5.The active agent becomes available when the pH-sensitive enteric layer dissolves at a higher pH in the GI tract, after a certain delayed time, or after the unit passes through the stomach. The preferred delay time is in the range of about 0.5 to about 6 hours, but more preferable is about 0.5 to about 4 hours.

For example, certain DR pellets may be coated with EUDRAGIT® L30D-55,which dissolves at about pH 5.5-6.0, i.e., in the upper intestines. In other embodiments, the DR pellets may be coated with EUDRAGIT® FS30D, which dissolves at about pH 7.0,i.e., in the lower intestine and colon.

As a variation of this embodiment, the XR pellet described above may be additionally coated with the enteric material to generate delayed and extended release (DXR) pellets. Such a dosage form is delayed release until the drug reaches non-acidic environment, such as the upper and/or lower intestine, and thereupon releasing drugs over an extended period of time.

ii) Extended Release Composition

The extended release pellets of RNAi compounds can be prepared in many different ways to achieve an extended release profile. For example, in certain embodiments, the subject extended release pellets can be prepared by coating drug layered inert pellets with release-controlling polymers. First, the inert pellet is coated with the drug layer, or a drug loaded granule is prepared, as described above. Then the active (drug loaded) pellet is coated with a release-controlling polymeric membrane. The release-controlling coating layer may be applied immediately outside the core (such as a drug-containing core or a drug-layered core), by conventional coating techniques, such as pan coating or fluid bed coating, using solutions of polymers in water or suitable organic solvents, or by using aqueous polymer dispersions. As an alternative embodiment, the release controlling membrane can separate additional drug layers on the core; for instance, after coating with the release controlling substance, another drug layer can be applied, which is followed by another release controlling layer, etc. Suitable materials for the release-controlling layer include EUDRAGIT® RL, EUDRAGIT® RS, cellulose derivatives such as ethylcellulose aqueous dispersions (AQUACOAT®, SURELEASE®), hydroxyethyl cellulose, hydroxypropyl cellulose, hydroxypropyl methylcellulose, polyvinylpyrrolidone, polyvinylpyrrolidone/vinyl acetate copolymer, OPADRY®), and the like. The thickness of the coating affects the release profile, and so this parameter can be used to customize the profile. The suggested coating levels are from about 1% to about 40%, about 5% to about 30% (w/w), or about 20% or about 25% in other embodiments.

In certain embodiments, it is desirable to further slow the process of drug release by providing a release-controlling coating around the tablet to produce an extended-release (XR) tablet. Such a coating may comprise a hydrophobic or water-insoluble polymer component such as ethylcellulose together with a hydrophilic or water-soluble pore-forming component such as HPMC. In addition, where tablets are to be subjected to an additional process step after compression, in particular a coating step, exposure to mechanical stresses is also greatly increased.

Where a starch is used having a tensile strength of at least about 0.15 kN cm$^{-2}$, preferably at least about 0.175 kN cm$^{-2}$, more preferably at least about 0.2 kN cm$^{-2}$, at a solid fraction representative of the tablet (e.g., about 0.75 to about 0.85), the composition is found to be especially suited to a high-speed tableting operation that includes a step of coating the tablet with a release-controlling layer.

Alternatives to ethylcellulose and HPMC as components of a release coating layer include other cellulosic polymers (e.g., methylcellulose, hydroxypropylcellulose, hydroxyethylcellulose, carboxymethylcellulose sodium, cellulose esters such as cellulose acetate, etc.), polyvinyl acetate, polyvinyl pyrrolidone, polymers and copolymers of acrylic acid and methacrylic acid and esters thereof, polyethylene glycol, carrageenan and other gums, etc.

A release-controlling layer, if present, typically constitutes about 1% to about 15%, preferably about 2.5% to about 10%, by weight of the tablet as a whole. The hydrophobic or water-insoluble component, preferably comprising ethylcellulose, typically constitutes about 1% to about 10%, preferably about 2% to about 7%, by weight of the tablet as a whole. The pore-forming component, preferably comprising HPMC, is typically present in an amount of about 5% to about 50%, preferably about 10% to about 40%, by weight of the water-insoluble or hydrophobic component.

The coating, if present, can optionally contain additional pharmaceutically acceptable excipients such as plasticizers, dyes, etc. Illustratively, a release-controlling layer in an amount of about 2.5% to about 5% by weight of the tablet core (i.e., the tablet weight excluding the coating) comprises an ethylcellulose-based material (e.g., SURELEASE® of Colorcon) and an HPMC-based pore-forming material (e.g., OPADRY® of Colorcon) in a weight ratio of about 3:1 to about 4:1. A release-controlling layer or coating is preferably applied at a relatively uniform thickness to provide even control of release rate of the active agent.

Alternatively or in addition, the sustained-release tablet of the invention comprises a nonfunctional coating. A nonfunctional coating can comprise a polymer component, for example HPMC, optionally with other ingredients, for example one or more plasticizers, colorants, etc. The term "nonfunctional" in the present context means having no substantial effect on release properties of the tablet, and does not imply that the coating serves no useful purpose. For example, such a coating can impart a distinctive appearance to the tablet, provide protection against attrition during packaging and transportation, improve ease of swallowing, and/or have other benefits. A nonfunctional coating should be applied in an amount sufficient to provide complete coverage of the tablet. Typically an amount of about 1% to about 10%, more typically an amount of about 2.5% to about 5%, by weight of the tablet as a whole, will be found suitable.

Uncoated tablets and cores of coated tablets of the invention can optionally contain one or more pharmaceutically acceptable excipients in addition to the starch and hydrophilic polymer components described above. Such excipients include without limitation glidants and lubricants. Other conventional excipients known in the art can also be included. A glidant can be used to improve powder flow properties prior to and during tableting and to reduce caking. Suitable glidants include colloidal silicon dioxide, magnesium trisilicate, powdered cellulose, starch, talc, tribasic calcium phosphate and the like. In certain embodiments, colloidal silicon dioxide is included as a glidant in an amount up to about 2%, preferably about 0.2% to about 0.6%, by weight of the tablet. A lubricant can be used to enhance release of a tablet from apparatus on which it is formed, for example by preventing adherence to the face of an upper punch ("picking") or lower punch ("sticking"). Suitable lubricants include magnesium stearate, calcium stearate, canola oil, glyceryl palmitostearate, hydrogenated vegetable oil, magnesium oxide, mineral oil, poloxamer, polyethylene glycol, polyvinyl alcohol sodium benzoate, sodium lauryl sulfate, sodium stearyl fumarate, stearic acid, talc, hydrogenated vegetable oil, zinc stearate and the like. In certain embodiments, magnesium stearate is included as a lubricant in an amount of about 0.1% to about 1.5%, preferably about 0.3% to about 1%, by weight of the tablet.

The invention also provides a method for making the pharmaceutical compositions with one or more features as described above. In some embodiments, the invention provides a method for using the pharmaceutical compositions with one or more features as described herein, in treating diseases and conditions including, but not limited to, macular degeneration, atherosclerosis, osteoporosis, immune inflammation (including arthritis, asthma, Crohn's disease, inflammatory bowel disease, type I diabetes, type II diabetes, multiple sclerosis, artherosclerosis), non-immune inflammation, tuberculosis, multiple sclerosis, arthritis, chronic obstructive pulmonary disease (COPD), and Alzheimer's disease. Further, methods for treating disease states associated with activation of innate immune system signaling are provided in accordance with other aspects of the present invention. Diseases may be, for example, sepsis and septic shock, neurodegeneration, neutrophilic alveolitis, asthma, hepatitis, inflammatory bowel disease, ischemia/reperfusion, septic shock, glomerulonephritis, rheumatoid arthritis or Crohn's disease.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like. Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

In other embodiments, the pharmaceutical composition can be prepared as a nutraceutical, i.e., in the form of, or added to, a food (e.g., a processed item intended for direct consumption) or a foodstuff (e.g., an edible ingredient intended for incorporation into a food prior to ingestion). Examples of suitable foods include candies such as lollipops, baked goods such as crackers, breads, cookies, and snack cakes, whole, pureed, or mashed fruits and vegetables, beverages, and processed meat products. Examples of suitable foodstuffs include milled grains and sugars, spices and other seasonings, and syrups. The particulate delivery systems described herein are preferably not exposed to high cooking temperatures for extended periods of time, in order to minimize degradation of the compounds.

A pharmaceutical composition of the invention can be prepared, packaged, or sold in a formulation suitable for pulmonary administration via the buccal cavity. Such compositions are conveniently in the form of dry powders for administration using a device comprising a dry powder reservoir to which a stream of propellant can be directed to disperse the powder or using a self-propelling solvent/powder-dispensing container such as a device comprising the particulate delivery system suspended in a low-boiling propellant in a sealed container. Dry powder compositions may include a solid fine powder diluent such as sugar and are conveniently provided in a unit dose form. Low boiling propellants generally include liquid propellants having a boiling point below 65 degrees F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the particulate delivery system).

Pharmaceutical compositions of the invention formulated for pulmonary delivery can also provide the active ingredient in the form of droplets of a suspension. Such formulations can be prepared, packaged, or sold as aqueous or dilute alcoholic suspensions, optionally sterile, comprising the particulate delivery system, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) particulate delivery system, the balance comprising an orally dissolvable or degradable composition and, optionally, one or more of the additional ingredients described herein. Alternately, formulations suitable for buccal administration can comprise a powder or an aerosolized or atomized solution or suspension comprising the particulate delivery system.

Equivalents

Those skilled in the art will recognize, or be able to ascertain using no more than routine experimentation, many equivalents to the specific embodiments of the invention described herein. Such equivalents are intended to be encompassed by the following claims. The entire contents of all patents, published patent applications and other references cited herein are hereby expressly incorporated herein in their entireties by reference.

We claim:

1. A delivery system for delivering an RNAi construct to a phagocytic cell and inhibiting expression of a target gene in the phagocytic cell, comprising an RNAi construct and a phagocytic cell-targeting moiety,
    wherein the RNAi construct is a double-stranded RNA (dsRNA) construct of 25-30 nucleotides in length, comprising:
    (1) a sense strand having a 5'-end and a 3'-end, wherein the 5'-end 12 nucleotides and the 3'-end 10 nucleotides of the sense strand comprise 2'-modified ribose sugars and,
    (2) an antisense strand having a 5'-end and a 3'-end, which hybridizes to the sense strand,
    wherein the phagocytic cell-targeting moiety comprises beta-glucan, and wherein the RNAi construct inhibits expression of the target gene in the phagocytic cell.

2. The delivery system of claim 1, wherein the dsRNA construct is blunt-ended.

3. The delivery system of claim 1, wherein each end of the sense strand comprises non-hydrolyzable internucleotide linkages.

4. The delivery system of claim 1, wherein the 2'-modified ribose sugars are 2'-O-alkyl nucleotides, 2'-deoxy-2'-fluoro nucleotides, 2'-deoxy nucleotides, 2'-H (deoxyribonucleotides), or combination thereof.

5. The delivery system of claim 4, wherein the 2'-O-alkyl nucleotides are 2'-O-methyl nucleotides or 2'-O-allyl nucleotides.

6. The delivery system of claim 1, wherein the antisense strand comprises a 2'-O-methyl modified nucleotide at the 2nd nucleotide on the 5'-end of the antisense strand and no other modified nucleotides or the antisense strand comprises at least four consecutive 2'-O-methyl modified 3'-end nucleotides with phosphothioate linkages.

7. The delivery system of claim 6, wherein the dsRNA has enhanced target specificity or reduced off-target silencing compared to a similar construct without the 2'-modification at said position(s).

8. The delivery system of claim 1, wherein the sense strand of the dsRNA comprises a mismatch nucleotide at the 2nd nucleotide from the 3'-end of the sense strand and/or the last 2nd-8th nucleotides at the 3'-end of the sense strand mismatch their corresponding antisense strand nucleotides.

9. The delivery system of claim 1, wherein the dsRNA has improved stability in serum and/or cerebral spinal fluid compared to an unmodified dsRNA having the same sequence and/or the dsRNA does not induce interferon response in primary cells.

10. The delivery complex of claim 1, wherein the phagocytic cell-targeting moiety further comprises one or more ligands for phagocytic cell receptor(s).

11. The delivery system of claim 1, wherein the antisense strand is unmodified.

12. A pharmaceutical composition comprising the delivery system of claim 1, and a pharmaceutically acceptable excipient.

13. A method of treating an individual for a disease condition associated with a phagocytic cell defect, comprising administering to the individual a delivery system of claim 1, wherein the RNAi construct antagonizes the function of a target gene causing the disease condition.

14. The method of claim 13, wherein the disease condition is: macular degeneration, osteoporosis, non-immune inflammation, chronic obstructive pulmonary disease (COPD), Alzheimer's disease, sepsis and septic shock, neutrophilic alveolitis, hepatitis, inflammatory bowel disease, ischemia/reperfusion, glomerulonephritis, or rheumatoid arthritis.

15. A method for delivering an RNAi construct to a phagocytic cell in a subject, comprising:
    administering a delivery system complex to the subject, wherein the delivery system complex comprises an RNAi construct and a phagocytic cell-targeting moiety, wherein the RNAi construct is a double-stranded RNA (dsRNA) construct of 19-49 nucleotid in length, comprising:
    (1) a sense strand having a 5'-end and a 3'-end,
    wherein the 5'-end 12 nucleotides and the 3'-end 10 nucleotides of the sense strand are 2'-modified sugars, and,
    (2) an antisense strand having a 5'-end and a 3'-end, which hybridizes to the sense strand, and
    wherein the phagocytic cell-targeting moiety comprises beta-glucan.

16. The method of claim 15, wherein the phagocytic cell-targeting moiety further comprises one or more ligands for phagocytic cell receptor(s).

17. The method of claim 15, wherein the dsRNA construct is blunt-ended.

* * * * *